US008831293B2

(12) United States Patent
Wolf et al.

(10) Patent No.: US 8,831,293 B2
(45) Date of Patent: Sep. 9, 2014

(54) SYSTEM AND METHOD FOR STATISTICAL MAPPING BETWEEN GENETIC INFORMATION AND FACIAL IMAGE DATA

(75) Inventors: Lior Wolf, Herzliya (IL); Yonatan Donner, Mountain View, IL (US); Rona Schniberg, Elkana (IL)

(73) Assignee: MTS Investments Inc., Tortola (VG) (GB)

( * ) Notice: Subject to any disclaimer, the term of this patent is extended or adjusted under 35 U.S.C. 154(b) by 838 days.

(21) Appl. No.: 12/989,021

(22) PCT Filed: Apr. 21, 2009

(86) PCT No.: PCT/IL2009/000430
§ 371 (c)(1),
(2), (4) Date: May 5, 2011

(87) PCT Pub. No.: WO2009/130693
PCT Pub. Date: Oct. 29, 2009

(65) Prior Publication Data
US 2011/0206246 A1  Aug. 25, 2011

Related U.S. Application Data

(60) Provisional application No. 61/046,689, filed on Apr. 21, 2008.

(51) Int. Cl.
*G06K 9/00* (2006.01)
*G06F 19/24* (2011.01)
*G06F 19/26* (2011.01)
*G06F 19/18* (2011.01)
(52) U.S. Cl.
CPC ............... *G06F 19/24* (2013.01); *G06F 19/26* (2013.01); *G06F 19/18* (2013.01)
USPC ......................................................... 382/118

(58) Field of Classification Search
None
See application file for complete search history.

(56) References Cited

U.S. PATENT DOCUMENTS

| 7,308,123 B2* | 12/2007 | Fenrich et al. ................ 382/125 |
| 2006/0285770 A1* | 12/2006 | Lim et al. ..................... 382/276 |
| 2007/0219433 A1* | 9/2007 | Stupp ............................ 600/300 |
| 2008/0027756 A1* | 1/2008 | Gabriel et al. .................... 705/2 |
| 2008/0082466 A1* | 4/2008 | Meijer et al. .................... 706/12 |
| 2012/0301882 A1* | 11/2012 | Koster et al. ................. 435/6.11 |

* cited by examiner

*Primary Examiner* — Vikkram Bali
(74) *Attorney, Agent, or Firm* — Sughrue Mion, PLLC

(57) ABSTRACT

A method and system for statistical mapping between genetic information and facial image data including collecting a multiplicity of sets of genetic information and matching facial image data representing a multiplicity of individuals, representing the genetic information of each of the multiplicity of individuals as a first multidimensional representation, representing the facial image data of each of the multiplicity of individuals as a second multidimensional representation; and inferring correlative, non-causal, statistical relationships between the first multidimensional representations and the second multidimensional representations. A system and method for estimating the likelihood of donor-recipient transplant compatibility using facial images of potential donors, the method including inferring correlative, non-causal, statistical relationships, indicative of transplant compatibility, between multidimensional representations of facial image data of potential donors and a multidimensional representation of information relating to a potential recipient.

18 Claims, 8 Drawing Sheets

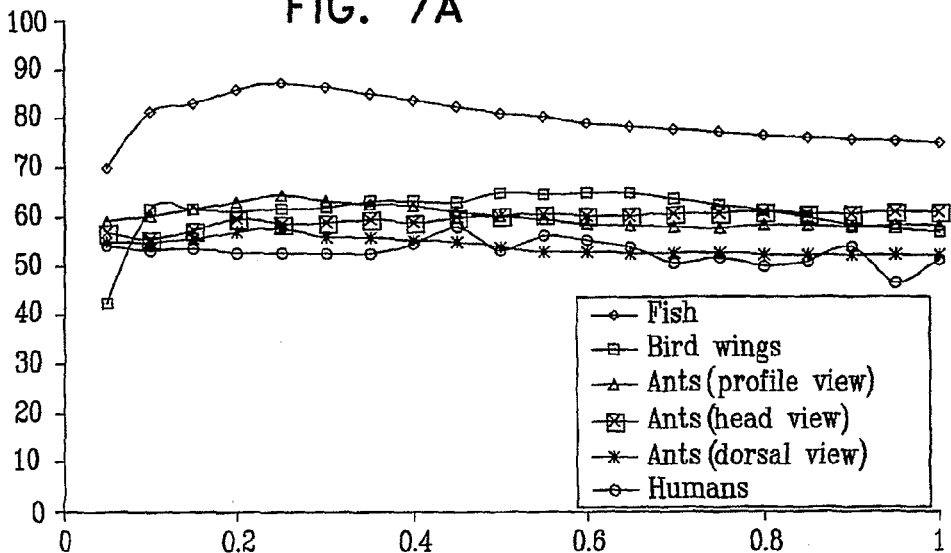
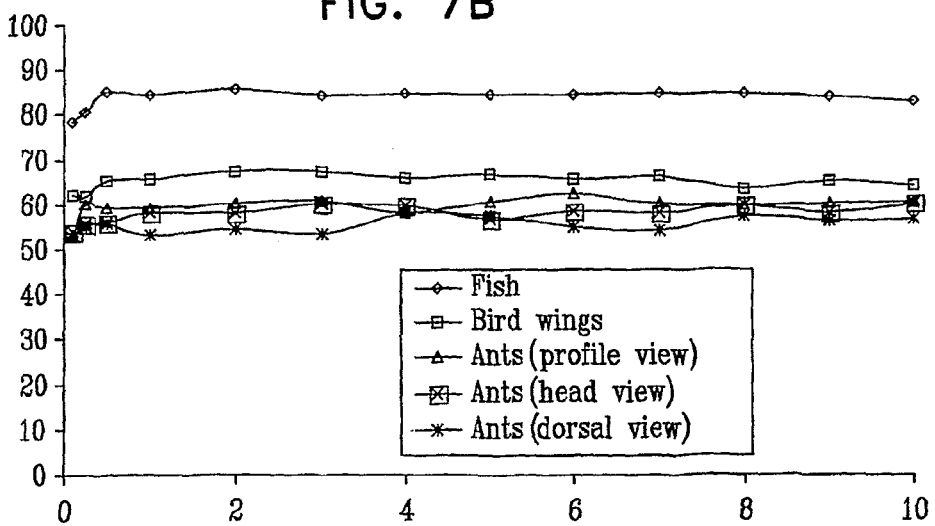

SYSTEM AND METHOD FOR STATISTICAL MAPPING BETWEEN GENETIC INFORMATION AND FACIAL IMAGE DATA

REFERENCE TO RELATED APPLICATIONS

Reference is hereby made to U.S. Provisional Patent Application 61/046,689, filed Apr. 21, 2008 and entitled DNA-BASED VISUAL IDENTIFICATION, the disclosure of which is hereby incorporated by reference and priority of which is hereby claims pursuant to 37 CFR 1.78(a)(4) and (5)(i).

FIELD OF THE INVENTION

The present invention relates to image processing generally and more particularly to image generation and image recognition from non-image data.

BACKGROUND OF THE INVENTION

The following publications are believed to represent the current state of the art:

Kobus Barnard et al., Matching words and pictures, Journal of Machine Learning Research, 3, 2003.

D L Duffy et al. A three-single-nucleotide polymorphism haplotype in intron 1 of OCA2 explains most human eye-color variation. Am J Hum Genet.; 80(2):241-52. 2007.

K. Chase, D. R. Carrier, F. R. Adler, T. Jarvik, E. A. Ostrander, T. D. Lorentzen, and K. G. Lark. Genetic basis for systems of skeletal quantitative traits: Principal component analysis of the canid skeleton. PNAS, 99:9930-9935, July 2002.

SUMMARY OF THE INVENTION

The present invention seeks to provide a system and methodology for image generation, image recognition and compatibility based on inferring correlative, non-causal, statistical relationships between images and genetic information.

Throughout the specification and claims, the term "genetic information" is defined as information derived from DNA, RNA or proteins.

There is thus provided in accordance with a preferred embodiment of the present invention a system and functionality for image generation using genetic information based on inferring non-causal (correlative) statistical relationships between images and genetic information in accordance with a preferred embodiment of the present invention.

In accordance with a preferred embodiment of the present invention, the image generation using genetic information includes statistical mapping functionality which collects a multiplicity of sets of genetic information and matching facial image data representing a multiplicity of individuals, preferably hundreds of individuals, more preferably thousands of individuals and most preferably hundreds of thousands or millions of individuals.

Preferably, the genetic information of each of the multiplicity of individuals is expressed or represented as a first multidimensional representation, such as a vector and the facial image data of each of the multiplicity of individuals is expressed or represented as a second multidimensional representation, such as a vector.

In accordance with a preferred embodiment of the present invention, a non-causal statistical correlation engine is employed to infer correlative, non-causal, statistical relationships between the first multidimensional representations and the second multidimensional representations. Resulting inferred models are stored by the system.

It is appreciated that the foregoing functionality may be considered to constitute a training phase which may be completed prior to deployment of the system for image generation or which may continue during the deployment phase of the functionality of the system.

In accordance with a preferred embodiment of the present invention, the first multidimensional representations are obtained by using one or more of the following methodologies:

representing nucleotide sequences of length n as vectors of length 4n wherein each element counts the number of occurrences of a specific nucleotide at a specific sequence location in the genetic information;

representing Short Tandem Repeat (STR) data of n loci as vectors of length 2n wherein each element depicts either the lower or the higher repetition number at one locus in the genetic information;

representing allele information of n loci, each having a multiplicity of $\gamma_i$, i=1 ... n alleles as vectors of length $$\sum_{i=1}^{n} \gamma_i$$

wherein each vector element denotes the number of times each allele is present in the genetic information; and representing the genetic information implicitly by providing a similarity function between the genetic information arising from every two individuals.

In accordance with a preferred embodiment of the present invention, the second multidimensional representations are obtained by using one or more of the following methodologies:

detection of a face region within the facial image data by using a learned template; and alignment of the face region by the detection of a set of fiducial points.

Preferably, the statistical mapping employed in the training phase employs at least one of the following algorithms:

regularized linear regression for obtaining a mapping between the genetic information and the face shape information; and regularized linear regression for obtaining a mapping between the genetic information and the facial texture information.

Preferably, the above-described training phase provides inferred models, which are results of statistical mapping between genetic information and facial image data including at least face shape information and preferably also facial texture information produced by inferring correlative, non-causal, statistical relationships between the first multidimensional representations of the genetic information and the second multidimensional representations of the facial image data for the multiplicity of individuals.

In the deployment phase, these results of statistical mapping are preferably applied to genetic information obtained from an individual not necessarily being an individual whose genetic information is used in the training phase, in a mapper which uses the inferred models. It is a particular feature of the present invention that the individual whose genetic information is mapped by the mapper need not be and normally is not one of the multiplicity of individuals whose genetic and image information are employed during the training phase.

The mapper provides facial image data including at least face shape information and preferably also facial texture information for the individual for whom genetic information is provided and a facial image is to be generated.

A facial image generator employs at least the face shape information and preferably also the facial texture information to generate a facial image of the individual whose genetic information is provided and whose facial image is to be generated.

In accordance with a preferred embodiment of the present invention, the facial image data corresponding to the image to be generated is also expressed or represented by a multidimensional representation, such as a vector.

Preferably the multidimensional representations of the facial image data of each of the multiplicity of individuals and of the individual whose genetic information is employed for image generation includes at least one of the following representations:
- a shape vector including a multiplicity of elements each indicating a location of a feature point or a contour point in the facial image data;
- a texture vector including a multiplicity of elements each indicating an image measurement at one image location of the facial image data.

The mapper preferably employs at least one of the following:
- linear regression models for recovering, generating or predicting the face shape information included in the facial image data of the individual whose genetic information is provided in the deployment phase; and
- linear regression models for recovering, generating or predicting the facial texture information included in the facial image data of the individual whose genetic information is provided in the deployment phase.

The mapper preferably employs at least one of the following:
- linear regression models for recovering the shape vector of the individual whose genetic information is provided in the deployment phase; and
- linear regression models for recovering the texture vector of the individual whose genetic information is provided in the deployment phase.

In accordance with a preferred embodiment of the present invention, the facial image generator employs thin plate spline warping of the facial texture information of whose genetic information is provided in the deployment phase in accordance with the face shape information of that individual.

Preferably, the facial image generator employs thin plate spline warping of the facial texture vector of whose genetic information is provided in the deployment phase in accordance with the locations encoded in the shape vector of that individual.

In accordance with another embodiment of the present invention there is provided a system and functionality for image recognition using genetic information based on inferring correlative, non-causal statistical relationships between images and genetic information.

In accordance with a preferred embodiment of the present invention, the image recognition using genetic information includes statistical mapping functionality which collects a multiplicity of sets of genetic information and matching facial image data representing a multiplicity of individuals, preferably hundreds of individuals, more preferably thousands of individuals and most preferably hundreds of thousands or millions of individuals.

Preferably, the genetic information of each of the multiplicity of individuals is expressed or represented as a first multidimensional representation, such as a vector, and the facial image data of each of the multiplicity of individuals is expressed or represented as a second multidimensional representation, such as a vector.

In accordance with a preferred embodiment of the present invention, a non-causal statistical correlation engine is employed to infer correlative, non-causal, statistical relationships between the first multidimensional representations and the second multidimensional representations. Preferably, causal statistical relationships are excluded. Resulting inferred models are stored by the system.

It is appreciated that the foregoing functionality may be considered to constitute a training phase which may be completed prior to deployment of the system for image generation or which may continue during the deployment phase of the functionality of the system.

In accordance with a preferred embodiment of the present invention, the first multidimensional representations are obtained by using one or more of the following methodologies:
- representing nucleotide sequences of length n as vectors of length 4n wherein each element counts the number of occurrences of each nucleotide at a specific sequence location in the genetic information;
- representing STR data of n loci as vectors of length 2n wherein each element depicts either the lower or the higher repetition number at one locus in the genetic information;
- representing allele information of n loci, each having a multiplicity of $\gamma_i$, i=1 ... n alleles as vectors of length $$\sum_{i=1}^{n} \gamma_i$$

wherein each vector element denotes the number of times each allele is present in the genetic information; and
- representing the genetic information implicitly by providing a similarity function between the genetic information arising from every two individuals.

In accordance with a preferred embodiment of the present invention, the second multidimensional representations are obtained by using one or more of the following methodologies:
- detection of a face region within the facial image data by using a learned template; and
- alignment of the face region by the detection of a set of fiducial points.

Preferably, the above-described training phase provides inferred models, which are results of statistical mapping between genetic information and facial image data produced by inferring correlative, non-causal, statistical relationships between the first multidimensional representations of the genetic information and the second multidimensional representations of the facial image data for the multiplicity of individuals.

In the deployment phase, these results of statistical mapping are preferably applied to genetic information, obtained from an individual not necessarily being an individual whose genetic information is used in the training phase, in a mapper which uses the inferred models. It is a particular feature of the present invention that the individual whose genetic information is mapped by the mapper need not be and normally is not one of the multiplicity of individuals whose genetic and image information are employed during the training phase.

The mapper receives facial image data for a plurality of candidate persons and provides an output indicating which of the candidate persons has the greatest likelihood of being the individual whose genetic information is supplied to the mapper and thus selects the facial image of the individual from among the facial images of the plurality of candidate persons.

Preferably a likelihood score is also provided. It is appreciated that this embodiment provides a virtual line-up functionality which has a large number of applications, including forensic applications.

In accordance with a preferred embodiment of the present invention, the facial image data of each of the plurality of candidate persons is represented as a multidimensional representation.

Preferably, the multidimensional representation of the facial image data of each of the plurality of candidate persons employs at least one of the following algorithms:
  detection of a face region within the facial image data by using a learned template; and
  alignment of the face region by the detection of a set of fiducial points.

In accordance with a preferred embodiment of the present invention, the multidimensional representation of the facial image data of each of the plurality of candidate persons includes at least one of the following representations:
  a vector containing a multiplicity of histograms of image gradients at a multiplicity of image locations; and
  a vector containing a multiplicity of histograms of local-binary-patterns obtained at a multiplicity of image locations.

Preferably, the inferring of statistical relationships employs at least one of the following algorithms: Canonical Correlation Analysis; Kernel Canonical Correlation Analysis; Nearest Neighbor Transfer; Generalized Nearest Neighbor Transfer; Inverse Nearest Neighbor Transfer; Inverse Generalized Nearest Neighbor Transfer; identification based on the structure of recovered phylogenetic trees and statistical classifier learning of multidimensional representations each containing information from the first multidimensional representation and the second multidimensional representation.

This statistical learning classifies vectors which are a concatenation of a genetic information vector and a genetic vector.

Preferably, selection of the facial image of the individual from among the facial images of the plurality of candidate persons employs at least one of the following methods:
  transformation of the facial image data and the genetic information using transformations obtained by employing Canonical Correlation Analysis;
  transformation of the facial image data and the genetic information using transformations obtained by employing Kernel Canonical Correlation Analysis;
  selection based on minimal $D_{L_1}$ distance;
  selection based on minimal $D_{CoL_1}$ distance;
  selection based on minimal $D_{L_2}$ distance;
  selection based on minimal $D_{CoL_2}$ distance;
  selection based on minimal $D_C$ distance;
  selection based on minimal $D_{CC}$ distance;
  selection based on the Nearest Neighbor Transfer decision rule;
  selection based on the Generalized Nearest Neighbor Transfer decision rule;
  selection based on the Inverse Nearest Neighbor Transfer decision rule;
  selection based on the Inverse Generalized Nearest Neighbor Transfer decision rule;
  selection based on examining the genetic information obtained from the individual and the facial images of the plurality of persons within the context of phylogenetic trees constructed from the first multidimensional representations of the genetic information and the second multidimensional representations of the facial image data for the multiplicity of individuals; and
  selection based on applying classification rules to multidimensional representations each containing information from the first multidimensional representation and the second multidimensional representation.

In accordance with another preferred embodiment of the present invention, image-based non-invasive transplant compatibility screening based on inferring correlative, non-causal, statistical relationships between images of compatible persons includes statistical mapping functionality which collects a multiplicity of sets of facial image data representing a multiplicity of pairs of individuals including many pairs of individuals who are known to be mutually transplant compatible and many pairs of individuals who are known to be mutually transplant incompatible. Preferably, image data on hundreds such compatible and incompatible pairs of individuals are employed in a training phase, more preferably thousands of such pairs of individuals and most preferably hundreds of thousands or millions of such pairs of individuals.

Preferably, the facial image data of each of the multiplicity of pairs of individuals is expressed or represented as multidimensional representation, such as a vector.

In accordance with a preferred embodiment of the present invention, a non-causal statistical correlation engine is employed to infer correlative, non-causal, statistical relationships between the first multidimensional representations the transplant compatibility status of the respective pairs. Preferably, causal statistical relationships are excluded. Resulting inferred models are stored by the system.

It is appreciated that the foregoing functionality may be considered to constitute a training phase which may be completed prior to deployment of the system for image-based non-invasive transplant compatibility screening or which may continue during the deployment phase of the functionality of the system.

In accordance with a preferred embodiment of the present invention, the multidimensional representations of facial image data are obtained by using one or more of the following methodologies:
  detection of a face region within the facial image data by using a learned template; and
  alignment of the face region by the detection of a set of fiducial points.

Generally stated, indicating the likelihood of donor-recipient transplant compatibility using facial images of potential donors and of a potential recipient preferably includes:
  representing facial image data of each of a multiplicity of the potential donors and of the potential recipient as multidimensional representations; and
  inferring correlative, non-causal, statistical relationships, indicative of transplant compatibility, between the multidimensional representations of the potential donors and the multidimensional representation of the potential recipient.

More particularly, estimating the likelihood of donor-recipient transplant compatibility using facial images of potential donors and of a potential recipient involves:
  collecting a multiplicity of facial image data pairs representing a multiplicity of pairs of individuals known to be transplant compatible or transplant incompatible;

representing the facial image data of each of the multiplicity of individuals as pairs of multidimensional representations;

inferring correlative, non-causal, statistical relationships between the pairs of multidimensional representations that indicate the likelihood of transplant compatibility of each associated pair of individuals; and employing correlative, non-causal, statistic relationships to estimate the likelihood of compatibility of multiple potential donors to a predetermined recipient, when the predetermined recipient and the multiple potential donors are represented by facial image data, wherein the multiple potential donors and the predetermined recipient are not necessarily among the multiplicity of pairs of individuals and normally are not among the multiplicity of pairs of individuals.

Preferably, the multiplicity of individuals known to be transplant compatible or transplant incompatible are identified by at least one of the following methods:
 examining human leukocyte antigen (HLA) types by Serotyping;
 using Gene Sequencing of HLA genes to determine HLA compatibility;
 performing Sequence-Specific Primed Polymerase Chain Reaction (PCR-SSP) HLA Typing; and
 estimating compatibility by means of recovering HLA Haplotypes.

In accordance with a preferred embodiment of the present invention, the multidimensional representation of the facial image data of each of the multiplicity of individuals includes at least one of the following representations:
 a vector containing a multiplicity of histograms of image gradients at a multiplicity of image locations; and
 a vector containing a multiplicity of histograms of local-binary-patterns obtained at a multiplicity of image locations.

Preferably, the inferring of non-causal (correlative) statistical relationships employs Supervised Distance Metric Learning which is preferably applied to the vectors.

In accordance with an embodiment of the present invention, the likelihood of donor-recipient transplant compatibility is indicated using facial images of potential donors and genetic information of a potential recipient by:
 collecting information representing a multiplicity of pairs of individuals known to be transplant compatible or transplant incompatible, wherein the information includes genetic information regarding one individual of the pair and facial image data regarding the other individual of the pair;
 representing the genetic information of each of the one individual of each pair of the multiplicity of pairs individuals and of the potential recipient as a first multidimensional representation;
 representing the facial image data of each of the other individual of each pair of the multiplicity of pairs of individuals and of each of the potential donors as a second multidimensional representation;
 providing results of statistical relationships between genetic information and facial image data produced by inferring correlative, non-causal, statistical relationships between first multidimensional representations of the genetic information and second multidimensional representations of the facial image data for a multiplicity of individuals, not necessarily including the potential recipient and the potential donors; and
 applying the results of the statistical relationships to genetic information obtained from the potential recipient and to the facial images of the potential donors, thereby to estimate the likelihood of donor-recipient transplant compatibility of each of the potential donors with the potential recipient.

In accordance with a preferred embodiment of the present invention, the first multidimensional representations are obtained by using one or more of the following methodologies:
 representing nucleotide sequences of length n as vectors of length 4n wherein each element counts the number of occurrences of each nucleotide at a specific sequence location in the genetic information;
 representing STR data of n loci as vectors of length 2n wherein each element depicts either the lower or the higher repetition number at one locus in the genetic information;
 representing allele information of n loci, each having a multiplicity of $\gamma_1$, i=1 ... n alleles as vectors of length $$\sum_{i=1}^{n} \gamma_i$$

wherein each vector element denotes the number of times each allele is present in the genetic information; and
 representing the genetic information implicitly by providing a similarity function between the genetic information arising from every two individuals.

Preferably, the second multidimensional representation employs at least one of the following algorithms:
 detection of a face region within the facial image data by using a learned template; and
 alignment of the face region by the detection of a set of fiducial points, and
 the second multidimensional representation includes at least one of the following representations:
 a vector containing a multiplicity of histograms of image gradients at a multiplicity of image locations; and
 a vector containing a multiplicity of histograms of local-binary-patterns obtained at a multiplicity of image locations.

In accordance with a preferred embodiment of the present invention, providing results of statistical relationships employs at least one of the following algorithms:
 Canonical Correlation Analysis;
 Kernel Canonical Correlation Analysis;
 Nearest Neighbor Transfer;
 Generalized Nearest Neighbor Transfer;
 Inverse Nearest Neighbor Transfer;
 Inverse Generalized Nearest Neighbor Transfer;
 identification based on the structure of recovered phylogenetic-trees; and
 statistical classifier learning of multidimensional representations each containing information from the first multidimensional representation and the second multidimensional representation.

Preferably, applying the results of the statistical relationships employs at least one of the following methods:
 transformation of the facial image data and the genetic information using transformations obtained by employing Canonical Correlation Analysis;
 transformation of the facial image data and the genetic information using transformations obtained by employing Kernel Canonical Correlation Analysis;
 selection based on minimal $D_{L_1}$ distance;
 selection based on minimal $D_{CoL_1}$ distance;
 selection based on minimal $D_{L_2}$ distance;
 selection based on minimal $D_{CoL_2}$ distance;

selection based on minimal $D_C$ distance;
selection based on minimal $D_{CC}$ distance;
selection based on the Nearest Neighbor Transfer decision rule;
selection based on the Generalized Nearest Neighbor Transfer decision rule;
selection based on the Inverse Nearest Neighbor Transfer decision rule;
selection based on the Inverse Generalized Nearest Neighbor Transfer decision rule;
selection based on examining the genetic information obtained from the potential recipient and the facial images of the potential donors within the context of phylogenetic trees constructed from the first multidimensional representations and the second multidimensional representations for the multiplicity of pairs; and
selection based on applying classification rules to multidimensional representations each containing information from the first multidimensional representation obtained from the genetic information of the potential recipient and each of the second multidimensional representation obtained from the facial image data of the potential donors.

In accordance with a preferred embodiment of the present invention, the multiplicity of individuals known to be transplant compatible or transplant incompatible are identified by at least one of the following methods:
examining human leukocyte antigen (HLA) types by Serotyping;
using Gene Sequencing of HLA genes to determine HLA compatibility;
performing PCR-SSP HLA Typing; and
estimating compatibility by means of recovering HLA Haplotypes.

There is also provided in accordance with a preferred embodiment of the present invention a system and functionality for image-based and genetic information-based non-invasive transplant compatibility screening based on inferring correlative, non-causal, statistical relationships between images and information of a multitude of types in accordance with a preferred embodiment of the present invention.

In accordance with a preferred embodiment of the present invention, there is provided image-based non-invasive transplant compatibility screening based on inferring correlative, non-causal, statistical relationships between images and genetic information of compatible persons. This embodiment employs statistical mapping functionality which collects a multiplicity of sets of genetic information and facial image data representing a multiplicity of pairs of individuals including many pairs of individuals who are known to be mutually transplant compatible and many pairs of individuals who are known to be mutually transplant incompatible. Preferably data on hundreds of such compatible and incompatible pairs of individuals, more preferably thousands of such pairs of individuals and most preferably hundreds of thousands or millions of such pairs of individuals, is employed in a training phase.

In accordance with a preferred embodiment of the present invention, multiple types of information relating to one member of each of the multiplicity of pairs of individuals is expressed or represented as a set of multidimensional representations, such as a set of vectors, and the facial image data of the other member of each of the multiplicity of pairs of individuals is expressed or represented as a multidimensional representation, such as a vector.

Preferably, the multiple types of information relating to one member of each of the multiplicity of pairs of individuals include any number of the following:
genetic information of one member;
facial image information of the other member; and
facial image data of the relatives of the one member.

In accordance with a preferred embodiment of the present invention, a non-causal statistical correlation engine is employed to infer correlative, non-causal, statistical relationships between the set of multidimensional representations obtained from the one member and the multidimensional representation obtained from the other member. Resulting inferred models are stored by the system.

It is appreciated that the foregoing functionality may be considered to constitute a training phase which may be completed prior to deployment of the system for image-based non-invasive transplant compatibility screening or which may continue during the deployment phase of the functionality of the system.

In the deployment phase, these results of statistical mapping are preferably applied to information of a multitude of types relating to a prospective transplant recipient, not necessarily being an individual whose information is used in the training phase, in a mapper which uses the inferred models. It is a particular feature of the present invention that the prospective transplant recipient, whose multiple types of information is mapped by the mapper, need not be and normally is not one of the multiplicity of individuals whose information of a multitude of types is employed during the training phase.

The mapper receives facial image data for a plurality of candidate transplant donors, and provides an output indicating which of the candidate donors have the greatest likelihood of being transplant compatible with the prospective transplant recipient, whose information of a multitude of types is supplied to the mapper and thus selects the facial image of the most compatible potential donors from among the facial images of the plurality of candidate donors.

Preferably a likelihood score is also provided.

Generally stated, the likelihood of donor-recipient transplant compatibility is estimated using facial images of potential donors and information of a multitude of types of a potential recipient by providing results of statistical relationships between information of a multitude of types and facial image data produced by inferring correlative, non-causal, statistical relationships between a set of multidimensional representations of the information of a multitude of types and multidimensional representations of the facial image data for a multiplicity of individuals, not necessarily including the prospective recipient and the potential donors.

In accordance with a preferred embodiment of the present invention, the likelihood of donor-recipient transplant compatibility is indicated using facial images of potential donors and information of a multitude of types of a potential recipient by:
collecting information representing a multiplicity of pairs of individuals known to be transplant compatible or transplant incompatible, wherein the information includes a multitude of information types regarding one individual of the pair and facial image data regarding the other individual of the pair;
representing the genetic information included in the multitude of information types of each of the one individual of each pair of the multiplicity of pairs of individuals and of the potential recipient as a first type of multidimensional representation;
representing the facial image data included in the multitude of information types of the one individual and of the potential recipient and of each of the other individual of each pair of the multiplicity of pairs of individuals and of each of the potential donors as a second type of multidimensional representation;

providing results of statistical relationships between information of a multitude of types and facial image data produced by inferring correlative, non-causal, statistical relationships between multidimensional representations of the first and second type and multidimensional representations of the second type for a multiplicity of individuals, not necessarily including the potential recipient and the potential donors; and applying the results of the statistical relationships to information of a multitude of types obtained from the potential recipient and to the facial images of the potential donors, thereby to estimate the likelihood of donor-recipient transplant compatibility of each of the potential donors with the potential recipient.

In accordance with a preferred embodiment of the present invention, the multidimensional representations of the first type are obtained by using one or more of the following methodologies:

representing nucleotide sequences of length n as vectors of length 4n wherein each element counts the number of occurrences of each nucleotide at a specific sequence location in the genetic information;

representing STR data of n loci as vectors of length 2n wherein each element depicts either the lower or the higher repetition number at one locus in the genetic information;

representing allele information of n loci, each having a multiplicity of $\gamma_i$, i=1 . . . n alleles as vectors of length $$\sum_{i=1}^{n} \gamma_i$$

wherein each vector element denotes the number of times each allele is present in the genetic information; and representing the genetic information implicitly by providing a similarity function between the genetic information arising from every two individuals.

Preferably, the multidimensional representations of the second type employ at least one of the following algorithms:

detection of a face region within the facial image data by using a learned template; and alignment of the face region by the detection of a set of fiducial points, and the second type of multidimensional representation includes at least one of the following representations:

a vector containing a multiplicity of histograms of image gradients at a multiplicity of image locations; and a vector containing a multiplicity of histograms of local-binary-patterns obtained at a multiplicity of image locations.

In accordance with a preferred embodiment of the present invention, the providing results of statistical relationships employs at least one of the following algorithms:

Canonical Correlation Analysis;
Kernel Canonical Correlation Analysis;
Nearest Neighbor Transfer;
Generalized Nearest Neighbor Transfer;
Inverse Nearest Neighbor Transfer;
Inverse Generalized Nearest Neighbor Transfer;
identification based on the structure of recovered phylogenetic-trees;
statistical classifier learning of multidimensional representations each containing information from the first multidimensional representation and the second multidimensional representation;
Supervised Distance Metric Learning; and
combining multiple statistical relationships employing supervised learning.

Preferably, applying the results of the statistical relationships employs at least one of the following methods:

transformation of the facial image data and the genetic information using transformations obtained by employing Canonical Correlation Analysis;

transformation of the facial image data and the genetic information using transformations obtained by employing Kernel Canonical Correlation Analysis;

selection based on minimal $D_{L_1}$ distance;
selection based on minimal $D_{CoL_1}$ distance;
selection based on minimal $D_{L_2}$ distance;
selection based on minimal $D_{CoL_2}$ distance;
selection based on minimal $D_C$ distance;
selection based on minimal $D_{CC}$ distance;
selection based on the Nearest Neighbor Transfer decision rule;
selection based on the Generalized Nearest Neighbor Transfer decision rule;
selection based on the Inverse Nearest Neighbor Transfer decision rule;
selection based on the Inverse Generalized Nearest Neighbor Transfer decision rule;
selection based on examining the genetic information obtained from the potential recipient and the facial images of the potential donors within the context of phylogenetic trees constructed from the first multidimensional representations and the second multidimensional representations for the multiplicity of pairs;
selection based on applying classification rules to multidimensional representations each containing information from the first multidimensional representation obtained from the genetic information of the potential recipient and each of the second multidimensional representation obtained from the facial image data of the potential donors;
selection based on learned Distance Metrics; and
selection based on combining multiple statistical relationships via a learned combination function.

In accordance with a preferred embodiment of the present invention, the multiplicity of individuals known to be transplant compatible or transplant incompatible are identified by at least one of the following methods:

examining human leukocyte antigen (HLA) types by Sero-typing;
using Gene Sequencing of HLA genes to determine HLA compatibility;
performing PCR-SSP HLA Typing; and
estimating compatibility by means of recovering HLA Haplotypes.

In this embodiment, various types of information obtained from the potential recipient are available during the search for a compatible donor. The types of information include genetic information, image information obtained from the recipient, and image information obtained from the relatives of the recipient. This information can be used for the task of visual likelihood compatibility estimation.

BRIEF DESCRIPTION OF THE DRAWINGS

The present invention will be understood and appreciated more fully from the following detailed description, taken in conjunction with the drawings in which:

FIGS. 7A and 7B are graphs depicting the effects of changing the values of relevant parameters on identification accuracy, with FIG. 7A showing Kernel Canonical Correlation Analysis performance with varying values of $\tau$ for fish, birds, ants, and humans and FIG. 7B showing Common Discriminant Feature Extraction (CDFE) performance with varying values of $\alpha$ for fish, birds, and ants.

DETAILED DESCRIPTION OF PREFERRED EMBODIMENTS

Figure 1:
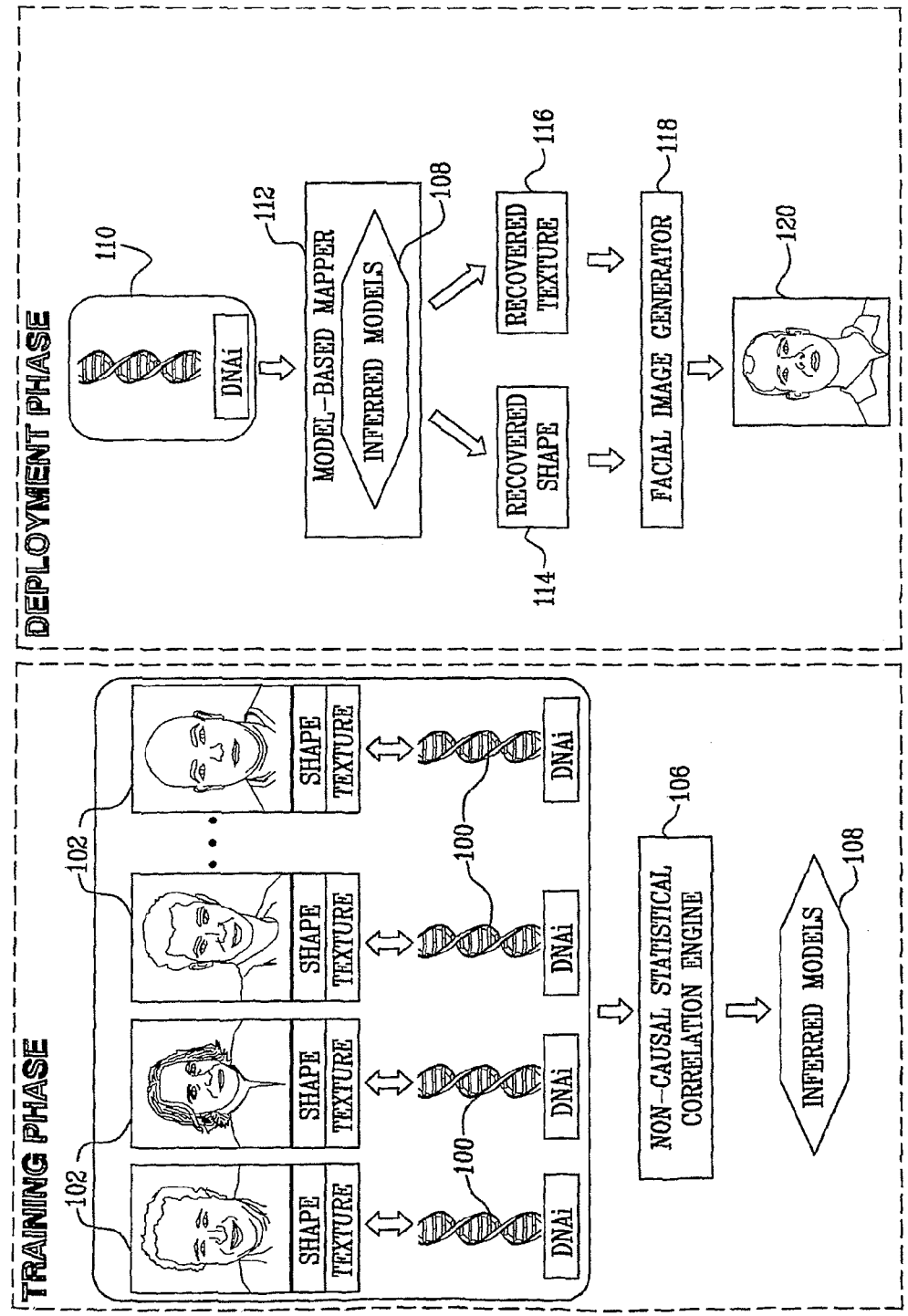
FIG. 1 is a simplified schematic illustration of a system and functionality for image generation using genetic information based on inferring correlative, non-causal, statistical relationships between images and genetic information in accordance with a preferred embodiment of the present invention.

Reference is now made to FIG. 1, which is a simplified schematic illustration of a system and functionality for image generation using genetic information based on inferring correlative, non-causal, statistical relationships between images and genetic information in accordance with a preferred embodiment of the present invention.

In accordance with a preferred embodiment of the present invention, the image generation using genetic information includes statistical mapping functionality which collects a multiplicity of sets of nucleotide sequence information 100 and matching facial image data 102 representing a multiplicity of individuals, preferably hundreds of individuals, more preferably thousands of individuals and most preferably hundreds of thousands or millions of individuals.

Preferably, the genetic information of each of the multiplicity of individuals is expressed or represented as a first multidimensional representation, such as a vector, and the facial image data of each of the multiplicity of individuals is expressed or represented as a second multidimensional representation, such as a vector.

In accordance with a preferred embodiment of the present invention, a non-causal statistical correlation engine 106 is employed to infer correlative, non-causal, statistical relationships between the first multidimensional representations and the second multidimensional representations. Preferably, causal statistical relationships are excluded. Resulting inferred models 108 are stored by the system.

It is appreciated that the foregoing functionality may be considered to constitute a training phase which may be completed prior to deployment of the system for image generation or which may continue during the deployment phase of the functionality of the system.

In accordance with a preferred embodiment of the present invention, the first multidimensional representations are obtained by using one or more of the following methodologies:
  representing nucleotide sequences of length n as vectors of length 4n wherein each element counts the number of occurrences of each nucleotide at a specific sequence location in the genetic information;
  representing STR data of n loci as vectors of length 2n wherein each element depicts either the lower or the higher repetition number at one locus in the genetic information;
  representing allele information of n loci, each having a multiplicity of $\gamma_i$, i=1 ... n alleles as vectors of length $$\sum_{i=1}^{n} \gamma_i$$

wherein each vector element denotes the number of times each allele is present in the genetic information; and
  representing the genetic information implicitly by providing a similarity function between the genetic information arising from every two individuals.

In accordance with a preferred embodiment of the present invention, the second multidimensional representations are obtained by using one or more of the following methodologies:
  detection of a face region within the facial image data by using a learned template; and
  alignment of the face region by the detection of a set of fiducial points.

Preferably, the statistical mapping employed in the training phase employs at least one of the following algorithms:
  regularized linear regression for obtaining a mapping between the genetic information and the face shape information; and
  regularized linear regression for obtaining a mapping between the genetic information and the facial texture information.

Preferably, the above-described training phase provides inferred models 108, which are results of statistical mapping between genetic information and facial image data including at least face shape information and preferably also facial texture information produced by inferring correlative, non-causal, statistical relationships between the first multidimensional representations of the genetic information and the second multidimensional representations of the facial image data for the multiplicity of individuals.

In the deployment phase, these results of statistical mapping are preferably applied to genetic information, designated by reference numeral 110, obtained from an individual not necessarily being an individual whose genetic information is used in the training phase, in a mapper 112 which uses the inferred models 108. It is a particular feature of the present invention that the individual whose genetic information 110 is mapped by mapper 112 need not be and normally is not one of the multiplicity of individuals whose DNA and image information are employed during the training phase.

Mapper 112 provides facial image data including at least face shape information 114 and preferably also facial texture information 116 for the individual for whom genetic information 110 is provided.

A facial image generator 118 employs at least the face shape information 114 and preferably also the facial texture information 116 to generate a facial image 120 of the individual whose DNA 110 is provided.

In accordance with a preferred embodiment of the present invention, the facial image data corresponding to image 120 is also expressed or represented by a multidimensional representation, such as a vector.

Preferably the multidimensional representations of the facial image data of each of the multiplicity of individuals and of the individual whose genetic information 110 is employed for image generation includes at least one of the following representations:

a shape vector including a multiplicity of elements each indicating a location of a feature point or a contour point in the facial image data; and a texture vector including a multiplicity of elements each indicating an image measurement at one image location of the facial image data.

Mapper 112 preferably employs at least one of the following:

linear regression models for recovering, generating or predicting the face shape information included in the facial image data of the individual whose DNA 110 is provided in the deployment phase; and linear regression models for recovering, generating or predicting the facial texture information included in the facial image data of the individual whose DNA 110 is provided in the deployment phase.

Mapper 112 preferably employs at least one of the following:

linear regression models for recovering the shape vector of the individual whose DNA 110 is provided in the deployment phase; and linear regression models for recovering the texture vector of the individual whose DNA 110 is provided in the deployment phase.

In accordance with a preferred embodiment of the present invention, the facial image generator 118 employs thin plate spline warping of the facial texture information of whose DNA 110 is provided in the deployment phase in accordance with the face shape information of that individual.

Preferably, the facial image generator 118 employs thin plate spline warping of the facial texture vector of whose DNA 110 is provided in the deployment phase in accordance with the locations of the shape vector of that individual.

It is a particular feature of the present invention that correlations between genotype and phenotype can be identified even in the absence of a direct causal relationship therebetween. The genes directly responsible for appearance are inherited together with other genes that are involved in completely different functions, or in no known functions at all, thus generating many intricate interdependencies that can be exploited statistically.

Learning the relationship between genotype and visual phenotype is based upon the successful prediction of appearance based on genetic markers, i.e., given a training set $\{M_i, P_i\}_{i=1}^{N}$ of N matching genetic markers and images, obtained from a group of individuals, and a marker of a new person $M_{new}$, to generate an image $\hat{P}_{new}$ such that $\hat{P}_{new}$ is a good approximation of the actual appearance of that person. This task is difficult due to the high dimensionality of the target space, e.g. the image.

Given a DNA sample of a person, such as a fetus, newborn, child or adult, it is useful for forensic, medical and other applications to estimate the appearance of that person at various stages of its life. Specifically, synthesis of the face of an individual from his/her genetic information is discussed below.

The synthesis of human faces requires the extraction of genetic information, parameterization of facial images, and mapping from genetic information to image parameters.

A sample of a person's biological matter is used to extract his genetic markers in a process called genotyping. Several technologies may be used for this extraction, including PCR (Polymerase Chain Reaction), DNA sequencing and DNA microarrays. During the first stage the genetic markers ($M_i$) are converted into vectors containing all measurement ($m_i$).

To describe DNA sequences as vectors, the sequences are first aligned to a reference sequence using sequence alignment techniques such as dynamic programming or BLAST (Basic Local Alignment Search Tool). For a given sample, and for most sequences, two aligned sequences are generated since non-mitochondrial sequences which are not on the X or Y chromosomes have a maternal copy and a paternal copy.

In the aligned sequence, in addition to having different nucleotides at the same location, some locations may be missing ("deletions"), or extra nucleotides may be inserted as various points ("insertions").

The aligned n nucleotides of each sequence (n is constant per dataset) are represented as a vector of dimension $n_m=4n+n'$ of integers of values 0, 1 or 2, where n' is the number of different insertions detected in all sequences in a large collection of aligned sequences. Different insertions vary with regard to their sequence, their location, or both. Accordingly, insertions of the same sequence of nucleotides at different loci are counted multiple times, as are insertions of a different sequence at the same locus.

Each element in the first 4n elements marks the appearance of a specific nucleotide (A, G, C or T) at a specific location in the aligned sequence. In this representation, the dot product of two gene vectors is the expected number of agreements between the sequences. If there are deletions in the given sequence as compared with a reference sequence, the given sequence does not contribute to any of the 4 elements corresponding to each of the deleted positions.

Each element in the remaining n' elements marks the appearance of a specific insertion out of the n' insertions identified in the data. For each insertion, a person can have no such insertion in his/her DNA, one such insertion, or two such insertions.

It is appreciated that it is sufficient to focus on the locations in which there are genetic polymorphisms in the data. Genetic polymorphisms are defined when at least two different sequences are found at the same location in a population. Locations at which all sequences have the same nucleotides give rise to constant vector elements and can be discarded.

An alternative representation based on the Kimura two-parameter model (K2P) [M. Kimura. A simple method for estimating evolutionary rates of base substitutions through comparative studies of nucleotide sequences. J Mol Evol, 16(2):111-120, December 1980.], which allows different probabilities for different kinds of nucleotide substitution (transitions and transversions), is also possible.

Some technologies, such as PCR, ASO (Allele-Specific Oligonucleotide) hybridization and microarray-based technologies, can extract single-nucleotide polymorphisms (SNPs) at various loci in the genome without direct sequencing. The same vector representation as described above can be used for this data as well.

In forensic applications, the usage of microsatellites such as STRs (Short Tandem Repeats) is of importance, since forensic labs are equipped to extract these genetic signatures. STRs from a number $\beta$ of loci are used producing $2\beta$ repetition numbers (having alleles from both parents). The repetition numbers are ordered such that in each pair arising from the same locus, the lower value is first and the higher value is second. Vectorization is done directly by creating vectors of $2\beta$ repetition numbers. Each element holds either the lower or the higher number of repeats for a specific microsatellite locus.

An alternative way to vectorize the STR data is to assign one element in the vector to each possible allele, i.e., if a certain locus has $\gamma$ possible values in the population then $\gamma$ vector elements are assigned to that locus. In this method, in the vector arising from a specific genetic signature, each value can be 0, if the allele is not present, 1, if the allele appears once, or 2, if there are two copies of that allele.

The statistical learning methods employed are not limited to the use of vectors. An alternative to vectorizing the genetic markers is to define a similarity measure between every two markers. The similarity function is based on distances between every two possible allele values at the same locus. The score between two genetic signatures (all loci) would be the sum of scores over all corresponding individual alleles. The distances between alleles are inferred, for example, from the probability of having those two alleles in the same person.

If genetic markers are presented by a similarity function, kernel methods are used instead of linear methods. For example, Kernel Ridge Regression [John Shawe-Taylor & Nello Cristianini, Kernel Methods for Pattern Analysis-Cambridge University Press, 2004] is used instead of Ridge Regression employed below.

A robust representation of faces may be obtained by factoring the face to shape and to texture as is done for example in [T. F. Cootes, G. J. Edwards, and C. J. Taylor. Active appearance models. IEEE Transactions on Pattern Analysis and Machine Intelligence, 23(6):681-685, 2001.]. In the present invention, both component of the face information are represented as vectors.

The shape model s(I) of a face image I is preferably defined as a list of anatomical points and evenly placed points at the contour of the visible part of the face and facial features inside it. The list contains points such as the corners of the eyes, points on the contour of the nose, points marking the shape of the eyebrows, and points on the contour of the face.

The shape model is estimated manually or automatically from each face image. Automatic processing is carried out using facial feature point detectors which are trained on a set of manually marked images, as described next.

Automatic detection of facial fiducial points has been achieved in the past in several ways [A. Lanitis, C. J. Taylor, and T. F. Cootes. A unified approach to coding and interpreting face images. In Proceedings of the International Conference on Computer Vision, pages 368-374, Washington, D.C., USA, 1995. IEEE Computer Society; L. Ding and A. M. Martinez. Precise detailed detection of faces and facial features. In Proceedings of IEEE Computer Vision and Pattern Recognition, 2008; L. Liang, R. Xiao, F. Wen, and J. Sun. Face alignment via component-based discriminative search. In ECCV '08: Proceedings of the 10th European Conference on Computer Vision, pages II: 72-85, 2008; Yi Zhou, Lie Gu, and Hong-Jiang Zhang. Bayesian tangent shape model: estimating shape and pose parameters via bayesian inference. Proceedings 2003 IEEE Computer Society Conference on, 1:I-109-I-116 vol. 1, June 2003.]. In the current system, the face region is first detected using a learned template. This template is learned using Support Vectors Machines from a large set of marked face images.

A Support Vectors Machine (SVM) is a supervised statistical learning algorithm that fits a linear or a generalized linear decision rule to training data [Nello Cristianini and John Shawe-Taylor. An Introduction to Support Vector Machines. Cambridge University Press, 2000.]. To detect faces, it is employed to distinguish between a large set of image patches of face images ("positive training sets") and a large set of image patches which are not of face images ("negative training sets"). The image patches are first represented as a vector containing histograms of image gradients at the vacancy of 9 points spread evenly around the image patch. Then SVM learns from the set of positive and negative vectors how to identify a face. Given a new image, all image patches, at several scales are classified by the model learned by the SVM. Local filtering is applied to prevent multiple detections of the same face.

The detected face region is represented as a collection of histograms of gradient orientations. A grid of 7×7 corners is placed over the face image. Each histogram is computed around one grid point of the detected face region. The entire detected face is represented by a vector containing the concatenation of all values from all histograms.

The locations of the points belonging to the shape model is estimated using a regression function learned from training data. Specifically, a Support Vector Machine Regressor is trained on a collection of training points on which fiducial points were manually marked. The Support Vector Machine Regressor [Nello Cristianini and John Shawe-Taylor. An Introduction to Support Vector Machines. Cambridge University Press, 2000.] is a supervised statistical learning algorithm that learns a linear or a generalized linear regression model. The learned model maps from the vector of concatenated histograms to the locations of the fiducial points.

The shape model is preferably used to warp the face to a standard shape. This is done by applying a thin-plate-spline warp [F. L. Bookstein. Principal warps: thin-plate splines and the decomposition of deformations. IEEE Transactions on Pattern Analysis and Machine Intelligence, 11(6):567-585, June 1989.] which is computed in accordance with the matching points in the shape model s(I) and in an average shape model ŝ. The latter is obtained by averaging the shape models of many sample face images.

The image values, including intensity values, color values or both, of the warped face image I define the texture model a(I). The image values are recorded only within the face region, which is the same for all warped images. Measurements outside the contour of the face are discarded.

It is possible to reduce the dimensionality of the shape and texture models. This is done by considering a collection of face images and employing dimensionality reduction algorithms such as the Principle Component Analysis (PCA) algorithm [T. Hastie, R. Tibshirani, and J. H. Friedman. The Elements of Statistical Learning. Springer, August 2001.].

The training set consists of genetic markers $M_i$ and matching face images $P_i$. The images are all taken at an age which is approximately the age in which one wishes to estimate the facial appearance. The images contain frontal faces taken under good illumination conditions. If the images are unaligned, face alignment techniques as described below are used. Similarly, for images of poor illumination, preprocessing is done to improve the image quality.

The genetic markers are vectorized to $m_i$, and the face images are automatically decomposed into shapes descriptors $s_i=s(P_i)$ and texture descriptors $a_i=a(P_i)$.

In order to alleviate the complexity of the mapping between DNA and face images, the DNA space is subdivided into multiple regions by employing clustering algorithms.

The samples are first divided into male and female samples. Then, in each of the two groups, a clustering algorithm such as the k-means algorithm [T. Hastie, R. Tibshirani, and J. H. Friedman. The Elements of Statistical Learning. Springer, August 2001.] is used to divide the samples into a number $\omega=400$ of subgroups $A_1, A_2, \ldots, A_{400}$. The clustering is based on the distances between every two genetic markers $\|mm_i - m_j\|$.

For each of the subgroups $A_k$ a linear regression model is trained which maps the vectors of the genetic markers to shape vectors. This is done by applying linear ridge regression [A. E. Hoerl and R. Kennard. Ridge regression: biased estimation for nonorthogonal problems. Technometrics, 12:55-67, 1970.] to learn from the training examples in $A_k$, the mapping between the genetic markers m, and the shape model $s_i$. The regularization value of the ridge regression is set to some parameter ($\eta_1=0.05$) times the largest eigenvalue of the covariance matrix of the genetic markers $m_i$ of the subgroup $A_k$.

Each subgroup $A_k$ is also subdivided into $\omega'=20$ smaller groups by means of clustering by the distances between the shape models $\|s_i - s_j\|$, thereby generating subgroups $A_k^1, A_k^2, \ldots, A_k^{20}$.

A second set of regression functions is then learned. These regression models map genetic vectors to texture vectors. This is done by applying linear ridge regression to learn, for each finer subgroup $A_k^j$, the mapping between the genetic markers $m_i$ and the texture model $a_i$. The regularization value of the ridge regression is set, to some parameter ($\eta_2=0.10$) times the largest eigenvalue of the covariance matrix of genetic vectors $m_i$ in the subgroup $A_k^j$.

Given a new genetic sample $M_{new}$ of an unseen individual, it is first converted to a vector $m_{new}$. The gender is estimated from the genetic information or otherwise. Then, out of the $\omega$ subgroups $A_1, A_2, \ldots, A_\omega$, of training samples of the same gender, the subgroup with the mean vector $$\overline{m}_k = \frac{1}{|A_k|} \sum_{i \in A_k} m_i$$

closest to in $m_{new}$ is chosen. Let the index of the selected subgroup be denoted as k*.

The regression model that maps genetic data to shape data for the selected subgroup $A_{k*}$ is applied to $m_{new}$, and the shape of the new person's face is estimated by the learned model $\hat{s}_{new}$.

Next, out of the finer subgroups $A_{k*}^1, A_{k*}^2, \ldots, A_{k*}^{\omega'}$, the subgroup with mean shape vector most similar to $\hat{s}_{new}$ is identified. Denote the index of the identified subgroup as j*. The mapping between the genetic vector and the texture vector of the selected finer subgroup $A_{k*}^{j*}$ is applied to $m_{new}$, and the texture of the unseen person's face is estimated by the learned model as $\hat{a}_{new}$.

The estimated image is synthesized by taking the recovered texture model $\hat{a}_{new}$, and warping it using the thin-plate-spline method from the standard shape to the recovered shape $\hat{s}_{new}$.

An alternative method to estimate the facial appearance for a new genetic sample $M_{new}$, is to defer the training until after the sample is given. This alternative method first selects from the training set the 1,000 individuals most similar genetically of the same gender, i.e., the 1,000 individual with minimal $\|m_i - m_{new}\|$ that have the same sex are first selected.

For these 1,000 individuals a linear regression model is trained which map the genetic vectors to shapes. This is done by applying linear ridge regression to learn, from these 1,000 training examples, the mapping between the genetic markers $m_i$ and the shape model $s_i$. The regularization value of the ridge regression is set to some parameter ($\eta_1=0.05$) times the largest eigenvalue of the covariance matrix of the 1,000 selected $m_i$ samples.

The learned model is applied to $m_{new}$, and the shape of the person is estimated by the learned model as $\hat{s}_{new}$.

Out of the 1,000 individuals closest genetically, a subset of 50 individuals with the most similar shape models to $\hat{s}_{new}$ is selected, i.e., all persons out of the 1,000 most similar genetically persons are ranked by the similarity of the shape model to the estimated one, and the 50 persons which are closest in their shape model are selected. The similarity between every two shape models is computed as the Euclidean distance between the vector representations.

A second regression function is then learned. This regression model maps genetic vectors to appearance vectors. This is done by applying linear ridge regression to learn, from the selected 50 training examples, the mapping between the genetic markers $m_i$ and the appearance model $a_i$. The regularization value of the ridge regression is set to some parameter ($\eta_2=0.10$) times the largest eigenvalue of the covariance matrix of the 50 selected genetic vectors $m_i$.

The learned model is applied to $m_{new}$, and the appearance of the person is estimated by the learned model as $\hat{a}_{new}$.

The estimated image is synthesized by taking the recovered appearance model $\hat{a}_{new}$, and warping it from the standard shape to the recovered shape $\hat{s}_{new}$ using the thin-plate-spline method.

It is appreciated that the above methods to synthesize human faces also apply to models of 3D human heads. Those too, can be separated into (3D) shape and texture, and parameterized in a similar way.

Figure 2:
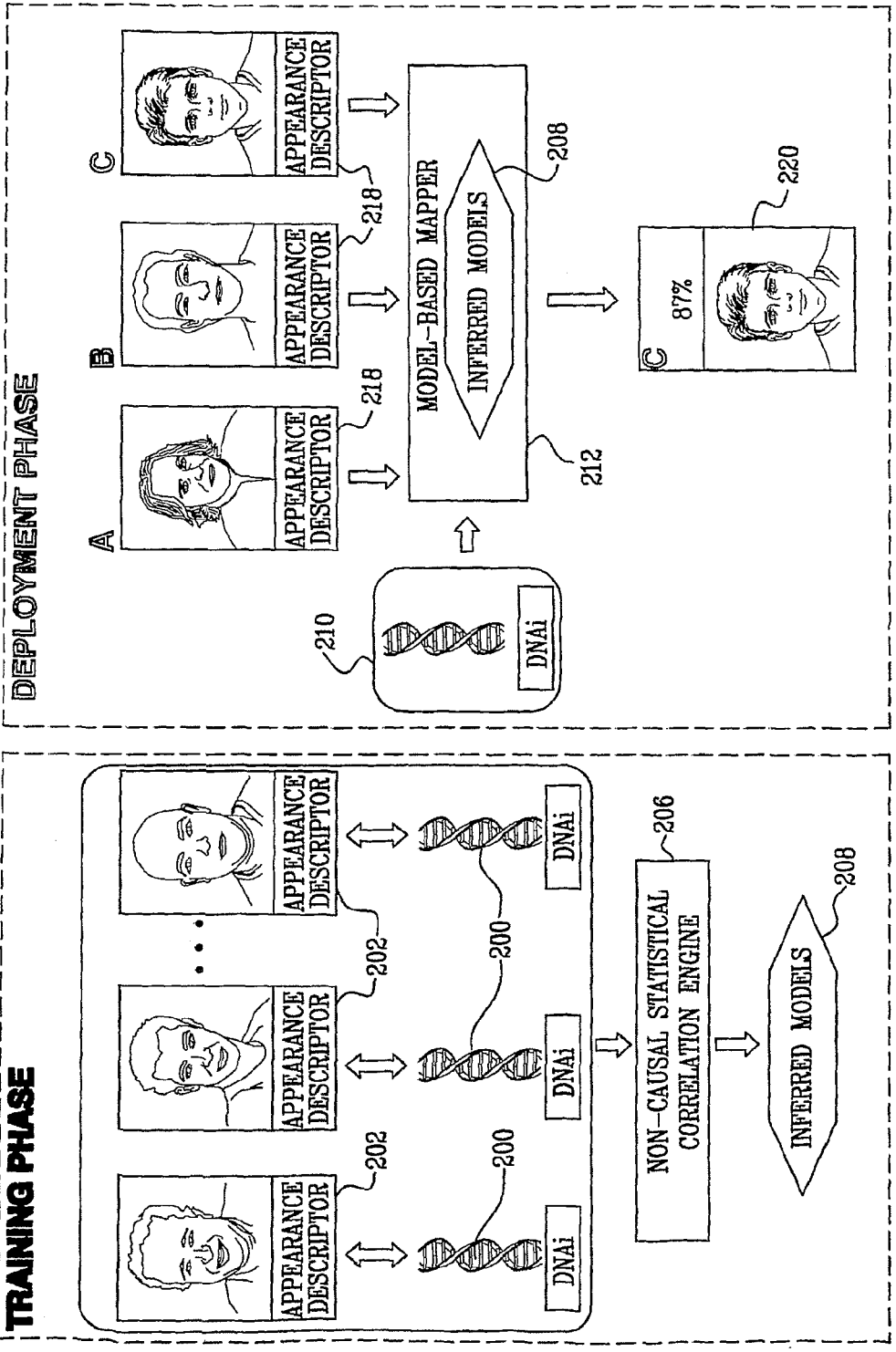
FIG. 2 is a simplified schematic illustration of a system and functionality for image recognition using genetic information based on inferring correlative, non-causal, statistical relationships between images and genetic information in accordance with a preferred embodiment of the present invention.

Reference is now made to FIG. 2, which is a simplified schematic illustration of a system and functionality for image recognition using genetic information based on inferring non-causal (correlative) statistical relationships between images and genetic information in accordance with a preferred embodiment of the present invention.

In accordance with a preferred embodiment of the present invention, the image recognition using genetic information includes statistical mapping functionality which collects a multiplicity of sets of genetic information 200 and matching facial image data 202 representing a multiplicity of individuals, preferably hundreds of individuals, more preferably thousands of individuals and most preferably hundreds of thousands or millions of individuals.

Preferably, the genetic information of each of the multiplicity of individuals is expressed or represented as a first multidimensional representation, such as a vector and the facial image data of each of the multiplicity of individuals is expressed or represented as a second multidimensional representation, such as a vector.

In accordance with a preferred embodiment of the present invention, a non-causal statistical correlation engine 206 is employed to infer correlative, non-causal, statistical relationships between the first multidimensional representations and the second multidimensional representations. Preferably, causal statistical relationships are excluded. Resulting inferred models 208 are stored by the system.

It is appreciated that the foregoing functionality may be considered to constitute a training phase which may be completed prior to deployment of the system for image generation or which may continue during the deployment phase of the functionality of the system.

In accordance with a preferred embodiment of the present invention, the first multidimensional representations are obtained by using one or more of the following methodologies:

representing nucleotide sequences of length n as vectors of length 4n wherein each element counts the number of occurrences of a specific nucleotide at a specific sequence location in the genetic information;

representing STR data of n loci as vectors of length 2n wherein each element depicts either the lower or the higher repetition number at one locus in the genetic information;

representing allele information of n loci, each having a multiplicity of $\gamma_i$, i=1 . . . n alleles as vectors of length $$\sum_{i=1}^{n} \gamma_i$$

wherein each vector element denotes the number of times each allele is present in the genetic information; and representing the genetic information implicitly by providing a similarity function between the genetic information arising from every two individuals.

In accordance with a preferred embodiment of the present invention, the second multidimensional representations are obtained by using one or more of the following methodologies:

detection of a face region within the facial image data by using a learned template; and alignment of the face region by the detection of a set of fiducial points.

Preferably, the above-described training phase provides inferred models 208, which are results of statistical relationships between genetic information and facial image data including produced by inferring correlative, non-causal, statistical relationships between the first multidimensional representations of the genetic information and the second multidimensional representations of the facial image data for the multiplicity of individuals.

In the deployment phase, these results of statistical mapping are preferably applied to genetic information, designated by reference numeral 210, obtained from an individual not necessarily being an individual whose genetic information is used in the training phase, in a mapper 212 which uses the inferred models 208. It is a particular feature of the present invention that the individual whose genetic information 210 is mapped by mapper 212 is need not be and normally is not one of the multiplicity of individuals whose genetic and image information are employed during the training phase.

Mapper 212 receives facial image data for a plurality of candidate persons, collectively designated by reference numeral 218, and provides an output 220 indicating which of the candidate persons has the greatest likelihood of being the individual whose genetic information 210 is supplied to mapper 212 and thus selects the facial image of the individual from among the facial images of the plurality of candidate persons.

Preferably a likelihood score is also provided. It is appreciated that the system and functionality of FIG. 2 provides a virtual line-up functionality which has a large number of applications, including forensic applications.

In accordance with a preferred embodiment of the present invention, the facial image data of each of the plurality of candidate persons is represented as a multidimensional representation.

Preferably, the multidimensional representation of the facial image data of each of the plurality of candidate persons employs at least one of the following algorithms:

detection of a face region within the facial image data by using a learned template; and alignment of the face region by the detection of a set of fiducial points.

In accordance with a preferred embodiment of the present invention, the multidimensional representation of the facial image data of each of the plurality of candidate persons includes at least one of the following representations:

a vector containing a multiplicity of histograms of image gradients at a multiplicity of image locations; and a vector containing a multiplicity of histograms of local-binary-patterns obtained at a multiplicity of image locations.

Preferably, the inferring of statistical relationships employs at least one of the following algorithms:

Canonical Correlation Analysis;

Kernel Canonical Correlation Analysis;

Nearest Neighbor Transfer;

Generalized Nearest Neighbor Transfer;

Inverse Nearest Neighbor Transfer;

Inverse Generalized Nearest Neighbor Transfer;

identification based on the structure of recovered phylogenetic-trees; and statistical classifier learning of multidimensional representations each containing information from the first multidimensional representation and the second multidimensional representation. This statistical learning classifies vectors which are a concatenation of a genetic information vector and an image vector.

Preferably, selection of the facial image of the individual from among the facial images of the plurality of candidate persons employs at least one of the following methods:

transformation of the facial image data and the genetic information using transformations obtained by employing Canonical Correlation Analysis;

transformation of the facial image data and the genetic information using transformations obtained by employing Kernel Canonical Correlation Analysis;

selection based on minimal $D_{L_1}$ distance;

selection based on minimal $D_{CoL_1}$ distance;

selection based on minimal $D_{L_2}$ distance;

selection based on minimal $D_{CoL_2}$ distance;

selection based on minimal $D_C$ distance;

selection based on minimal $D_{CC}$ distance;

selection based on the Nearest Neighbor Transfer decision rule;

selection based on the Generalized Nearest Neighbor Transfer decision rule;

selection based on the Inverse Nearest Neighbor Transfer decision rule;

selection based on the Inverse Generalized Nearest Neighbor Transfer decision rule;

selection based on examining the genetic information obtained from the individual and the facial images of the plurality of persons within the context of phylogenetic trees constructed from the first multidimensional representations of the genetic information and the second multidimensional representations of the facial image data for the multiplicity of individuals; and selection based on applying classification rules to multidimensional representations each containing information from the first multidimensional representation and the second multidimensional representation.

The embodiment of FIG. 2 is considered to be less demanding computationally than the embodiment of FIG. 1. The embodiment of FIG. 2 involves the task of identifying the matching face image out of k candidate images $P_1, \ldots, P_k$ given its genotype M, where the genetic marker and the species in the candidate images are all normally previously unseen.

It is appreciated that the ability to predict the image $\hat{P}$ that corresponds to the genetic marker M implies the ability to identify without difficulty the correct image as the one closest visually to $\hat{P}$. The converse is not true: statistical genotype-phenotype correlations are used in this embodiment to identify relations that are used to solve the selection task without necessarily providing the ability to synthesize an image.

In a virtual lineup application, suspects are identified based on DNA left in the crime scene. The DNA collected from the crime scene is matched against the face or other images of suspects captured by surveillance cameras nearby the crime scene, or to images obtained otherwise (e.g., from the police photo album, or to images of people with access to the crime scene, etc.). The DNA-to-image match of the best score, or the several matches of the highest scores suggest possible suspects.

The system and its functionality include two phases: a training stage and a deployment stage. During the training stage the system learns how to relate between genetic markers and images of a human population. During the deployment stage, queries can be sent to the system. Each query consists of a genetic signature of one person and several possible matching images and the system returns a matching score for each image. The higher the score, the more likely the image matches the given DNA signature.

During the training stage the system receives genetic signatures and face images of the same persons, i.e., the system receives pairs $(M_i, P_i)$, $i=1 \ldots N$, where $M_i$ is a set of genetic markers for person i (genetic signature), and $P_i$ is facial image of the same person. The system then learns to match genetic markers with face images. The learning is based on three components. First, the genetic markers are represented as a vector. Second, (in parallel to the first stage) the image is analyzed and represented as a vector. Third, statistical learning tools are used to relate the genetic signature to the face image.

During the training stage the genetic markers ($M_i$) are converted into vectors containing all measurement ($m_i$), as explained above. In forensic applications the usage of microsatellites or STRs is of importance, since forensic labs are equipped to extract these genetic signatures. In the experiments conducted for the construction of the current system, STRs from 10 loci are used, thus providing 20 repetition numbers (having alleles from both parents). The repetition numbers are ordered such that in each pair arising from the same locus, the lower value is first.

Vectorization is done by one of several methods. A direct vectorization may be carried out by creating vectors of 20 repetition numbers. Each element holds either the lower or the higher number of repeats for a specific microsatelite locus.

An alternative approach is to assign one element in the vector to each possible allele, i.e., if a certain locus has γ possible values in the population then γ vector elements are assigned to that locus. In this method, in the vector arising from a specific genetic signature, each value can be 0, if the allele is not present, 1, if the allele appears once, or 2, if there are two copies of that allele.

The statistical learning methods employed are not limited to the use of vectors. It is possible to not define vectors for each genetic marker, and instead to define a similarity measure between every two markers. The similarity function is based on distances between every two possible allele values at the same locus. The score between two genetic signatures (all loci) would be the sum of scores over all corresponding individual alleles. The scores assigned to every two alleles are inferred from the probability of having those two alleles in the same person.

If genetic markers are represented by a similarity function, kernel methods can be used instead of linear methods. For example, Kernel Canonical Correlation Analysis (CCA) can be used instead of Canonical Correlation Analysis, as explained below.

For the representation of facial images of the multiplicity of individuals used in the training phase and of facial images of the candidate persons employed in the deployment phase, a descriptor based approach is preferably employed. For each input image $P_i$ the image is first aligned and then represented as a vector $p_i$ encoding local appearance information at each point of the face.

The alignment is done either automatically or by manual alignment. In both cases it is based on recognizing in the image the location of a set of fiducial points such as the corners of the eyes, the corners of the mouth, and the tip of the nose. An affine geometric transformation is computed that brings the detected fiducial points to locations as close as possible to standard locations. These standard locations are computed as the mean location of the fiducial points over a large set of face images.

Automatic detection of facial fiducial points can be achieved in several ways [A. Lanitis, C. J. Taylor, and T. F. Cootes. A unified approach to coding and interpreting face images. In Proceedings of the International Conference on Computer Vision, pages 368-374, Washington, D.C., USA, 1995. IEEE Computer Society; L. Ding and A. M. Martinez. Precise detailed detection of faces and facial features. In Proceedings of IEEE Computer Vision and Pattern Recognition, 2008; L. Liang, R. Xiao, F. Wen, and J. Sun. Face alignment via component-based discriminative search. In ECCV '08: Proceedings of the 10th European Conference on Computer Vision, pages II: 72-85, 2008; Yi Zhou, Lie Gu, and Hong-Jiang Zhang. Bayesian tangent shape model: estimating shape and pose parameters via bayesian inference. Proceedings 2003 IEEE Computer Society Conference on, 1:I-109-I-116 vol. 1, June 2003.]. In the current system, the face region is first detected by using a template learned via a Support Vectors Machine Classifiers as explained above.

The detected face region is then represented as a collection of histograms of gradient orientations. A grid of 7×7 corners is placed over the face image. Each histogram is computed around one grid point of the detected face region. The entire detected face is represented by a vector containing the concatenation of all values from all histograms. The locations of fiducial points is estimated using a regression function learned from training data. Specifically a Support Vector Machine Regressor is trained as explained above on a collection of training points on which fiducial points were manually marked. The Support Vector Machine maps from the vector of concatenated histograms to the locations of the fiducial points.

A computed affine transformation, which aligns the locations of the detected fiducial points to standard locations is used to warp the entire image. This transformation is computed by minimizing the least squares distance between the transformed fiducial points and standard locations obtained by averaging many images as explained above.

The aligned image, e.g. the image after is was warped by the computed Affine transform, is represented by a vector which captures its appearance. The system combines several appearance descriptors into one long vector. One type of descriptors records the histograms of gradient orientation around grid points as above. Another type of descriptor records the histogram of Local Binary Patterns [T. Ahonen, A. Hadid, and M. Pietikainen. Face description with local binary patterns: Application to face recognition. IEEE Transactions on Pattern Analysis and Machine Intelligence, 28(12):2037-2041, December 2006.] at each grid cell. Local Binary Patterns are a local texture descriptor created by thresholding the intensity values around each image pixel by the value of that pixel, thereby marking which pixels are higher in values than the central pixel. These binary states (higher or not higher) are encoded as short binary strings. The frequency of each binary string at each cell grid is recorded in a histogram.

It is appreciated that more than one image per person can be used in both training and deployment. In training, the extra images can be added to the training set as more pairs of matching genetic signature and images, where each image of the same person produces one pair (the genetic signature is repeated). Alternatively, one face representation can be inferred from all images, as the mean value obtained from them.

After vectorization, the markers and images are represented as vectors, thereby obtaining a set of matching training vectors $(m_i, p_i)$, $i=1 \ldots N$, where $m_i$ is the genetics markers of person i (genetic signature) transformed into a vector, and $p_i$ is the vector of descriptors extracted from the facial image of the same person.

Later, at the deployment stage, an unseen genetic markers $M_{new}$ is provided which is represented as a vector $m_{new}$, and the task is to chooses out of a set of unseen face images $P_1$, $P_2$, ... $P_{new_k}$ the matching one. These candidate images would be vectorized as $p_1, p_2, \ldots p_{new_k}$.

In order to learn the matching between the vector representing the genetic signature and the vector representing the face image, various methods are used. Specifically, experimented have been conducted for the virtual line-up application using Canonical Correlation Analysis (CCA), Nearest Neighbor Transfer (NNT), and a generalized version of the NNT algorithm. Other suitable methods include the use of phylogenetic trees or binary classifiers for the matching task.

In Canonical Correlation Analysis (CCA) [H. Hotelling. Relations between two sets of variates. Biometrika, 28(3/4): 321-377, December 1936.], the samples of each dataset are first centered to have a zero mean vector value, then two transformations are found that cast genes and images to a common target vector-space such that the matching genes and images are transformed to similar vectors in the sense of maximal correlation coefficient. Additional constraints are that the components of the resulting vectors would be pairwise uncorrelated and of unit variance.

The CCA formulation is, therefore:

$$\max_{W_X, W_Y} \sum_{i=1}^{n} m_i^T W_X W_Y^T p_i, \text{ subject to}$$

$$\sum_{i=1}^{n} W_X^T m_i m_i^T W_X = \sum_{i=1}^{n} W_Y^T p_i p_i^T W_Y = I$$

The dimension of the target vector space is the minimum of the two dimensions $d_M$ and $d_P$ and is denoted by l. Thus $W_X$ is a matrix of dimensions $d_M \times l$ and $W_Y$ is of dimensions $d_P \times l$.

The training phase in the case of CCA produces the two matrices $W_X$ and $W_Y$.

Since the feature vectors for both genes and images are of dimensions significantly higher than the number of training samples, statistical regularization must be used to avoid overfitting. A regularized version of CCA suggested by [H. D. Vinod. Canonical ridge and econometrics of joint production. Journal of Econometrics, 4(2):147-166, May 1976.] is used. Generally, two regularization parameters need to be determined: $\eta_m$ and $\eta_p$. A single regularization parameter $\eta$ is used instead as follows. Let $X=[m_1 \, m_2 \ldots m_N]$ and $Y=[p_1 \, p_2 \ldots p_N]$, and denote by $\lambda_M, \lambda_P$ the largest eigenvalues of $XX^T$ and $YY^T$. The method sets $\eta_M = \eta \lambda_M$ and similarly for $\eta_P$. This way of choosing the regularization parameters is invariant to scale and can be used uniformly across all data sets.

CCA only examines linear transformations. To overcome this limitation, kernelized versions have been proposed (e.g. [F. R. Bach and M. I. Jordan. Kernel independent component analysis. J. Mach. Learn. Res., 3:1-48, 2003; David R. Hardoon and John Shawe-Taylor. Kcca for different level precision in content-based image retrieval. In Proceedings of Third International Workshop on Content-Based Multimedia Indexing, IRISA, Rennes, France, 2003.]). The use of Kernel CCA also enables the use of non-vectorial representations, in which instead of vectorizing the genetic markers (or the images), two similarity functions $K_M(M_i, M_j)$ (or $K_P(P_i, P_j)$) are defined such that given two genetic (visual) samples provide a similarity score. In this similarity score higher values mean more similar samples. For mathematical soundness, the similarity functions, which are known as kernels, should be positive definite kernels. However, in practice this is not strictly required.

Given two non-linear transformations $\phi: M \rightarrow \hat{M}$, $\psi: P \rightarrow \hat{P}$ to high-dimensional spaces, Kernel CCA solves a problem similar to CCA, where $m_i$ is replaced by $$\overline{\phi(m_i)} = \phi(m_i) - \frac{1}{N} \sum_{j=1}^{N} \phi(m_j)$$

and $p_i$ is replaced by $$\overline{\psi(p_i)} = \psi(p_i) - \frac{1}{N} \sum_{j=1}^{N} \psi(p_j)$$

If $\psi$ and $\phi$ satisfy certain conditions, the solution is efficiently obtained by employing the "kernel trick" which allows the solution to be found without explicitly evaluating $\phi$ and $\psi$. Rather, kernel functions $K_M: M \times M \rightarrow R$ and $K_P: P \times P \rightarrow R$ are used.

In some of the experiments done in the current system, Gaussian kernels are used:

$$K_M(m_1, m_2) = \exp\left(\frac{-\|m_1 - m_2\|^2}{2\sigma_M^2}\right)$$

$$K_P(p_1, p_2) = \exp\left(\frac{-\|p_1 - p_2\|^2}{2\sigma_P^2}\right).$$

$\sigma_M$ and $\sigma_P$ are Gaussian widths. The two widths are determined using a single parameter $\tau$ by setting $$\sigma_M = \tau\sqrt{\frac{2}{N(N-1)}\sum_{1\leq i<j\leq N}\|m_i - m_j\|^2}$$

and similarly for $\sigma_P$. Regularization is applied similarly to the Canonical Correlation Analysis above.

In the NNT method, the image of the most similar genetic marker to the query marker is used as a target image. All images in the virtual lineup are compared to this image, and the most similar image is selected.

Specifically, given a new genetic marker $m_{new}$, this method chooses out of the existing markers the closest one $$i^* = \underset{i=1}{\overset{N}{\operatorname{argmin}}}\|m_i - m_{new}\|$$

and selects the image $j^*$ most similar to the corresponding image $p_{i^*}$:

$$j^* = \underset{j=1}{\overset{k}{\operatorname{argmin}}}\|p_{new_j} - p_{i^*}\|$$

In the generalized NNT algorithm, given a genetic signature, the matching image or images of the most similar genetic signature or signatures are used as training examples for a model by which the face images are scored. More specifically, given a new genetic marker vector $m_{new}$, the method chooses out of the genetic vectors in the training set ($\{m_1, m_2, \ldots, m_N\}$) a certain number (a parameter $\alpha=3$) of the closest markers (those with minimal values of $\|m_i - m_{new}\|$).

The set of training pictures $\{p_1, p_2, \ldots, p_N\}$ is then divided into two classes. One class contains the face images that are matching to the $\alpha$ closest genetic signatures and the second class contains the rest of the images (N-$\alpha$ images). A Support Vector Machine Classifier is then trained to distinguish between the two classes. The image with the highest classification score (most likely to be positive according to the learned SVM decision rule) is selected out of all candidate images in the virtual line-up.

When genetic information available is limited in information quantity in comparison to the quality of the face images, for example, when STRs from 10 loci are employed, inverse forms of NNT and of generalized NNT are employed as well.

In Inverse Nearest Neighbor Transfer (INNT), for each candidate matching face image in the virtual line up the most similar face in the training set is found. The method then considers the corresponding genetic markers in the training set. One corresponding marker per candidate matching image. The distance of these corresponding training genetic market to the query genetic marker is used as a basis for a matching score.

More specifically, given the genetic marker vector $m_{new}$ and a set of face image vectors (possible suspects) $\{p_{new_1}, \ldots, p_{new_k}\}$, the method finds for each face image $p_{new_j}$ the closest training image:

$$a_j = \underset{j=1}{\overset{k}{\operatorname{argmin}}}\|p_i - p_{new_j}\|$$

The image is then assigned a score in accordance with the similarity between the matching training genetic marker vector in to $m_{a_j}$ to $m_{new}$:

$$\|m_{new} - m_{a_j}\|.$$

The image with the lowest distance is chosen.

Similarly, the inverse generalized NNT algorithm works by finding for each candidate image the set of $\alpha=3$ closet training images. The set of $\alpha$ matching genetic markers are used as a positive set, while the rest of the training genetic markers are used as a negative one. A support vector machine is trained to distinguish between the two classes. This is repeated for each candidate face image $\{p_{new_1}, \ldots, p_{new_k}\}$. The query genetic marker $m_{new}$ is then classified by each of the k classifiers. As a score for each candidate image, the classification outcome is used, i.e., the j-th score is high if the j-th classifier is likely to assign a positive label to $m_{new}$. The image with the highest score is then selected.

As an alternative, two forms of phylogenetic-tree based identification may be used for the matching task. In a preferred embodiment, both phylogenetic trees for the genotype and the phenotype are constructed using the UPGMA method [R. R. Sokal and C. D. Michner. A statistical method for evaluating systematic relationships. Univ. Kans. Sci. Bull, 38:1409-1438, 1958.].

In the first method (PT1), a phylogenetic tree is constructed using the UPGMA method for the pairs of genetic markers and images ($m_i$, $p_i$) in the training set, where the distances are determined by Euclidean distance between the vector representations of the genetic markers. A similar method can be obtained by replacing the roles of the genetic markers and images.

After the tree has been constructed, during deployment, given the new marker $m_{new}$, the node $v=(m_i, p_i)$ in the tree that minimizes $\|m_i - m_{new}\|$ is found, as well as the nodes $u_k=(m_{i_k}, p_{i_k})$ that minimize $\|p_{i_k} - p_{new_k}\|$ for each of the new images $\{p_{new_k}\}$. The chosen image $p_k$ is that for which the tree distance, measured as number of edges, between $v$ and $u_k$ is minimal.

The second method (PT2) is based on a similarity measure between phylogenetic trees, where the similarity between two trees is defined as the linear correlation between the two corresponding distance matrices [C. Goh, A. A. Bogan, M. Joachimiak, D. Walther, and F. E. Cohen. Co-evolution of proteins with their interaction partners. Journal of Molecular Biology, 299(2):283-293, June 2000]:

$$\frac{\sum_{i=1}^{N}\sum_{j=1}^{N}(D_{ij}^{M}-\overline{D}^{M})(D_{ij}^{P}-\overline{D}^{P})}{\sqrt{\sum_{i=1}^{N}\sum_{j=1}^{N}(D_{ij}^{M}-\overline{D}^{M})^{2}}\sqrt{\sum_{i=1}^{N}\sum_{j=1}^{N}(D_{ij}^{P}-\overline{D}^{P})^{2}}}$$

where $D^M$ and $D^P$ are matrices representing the genotype and phenotype distances, respectively, and $$\overline{D}^{M}=\frac{1}{n^{2}}\sum_{i=1}^{N}\sum_{j=1}^{N}D_{ij}^{M}$$

$$\overline{D}^{P}=\frac{1}{n^{2}}\sum_{i=1}^{N}\sum_{j=1}^{N}D_{ij}^{P}$$

It is appreciated that there is no need to compute the trees, since only the distance matrices are needed.

During deployment, the chosen image using this method maximizes, by searching over the unknown matching index k, this similarity between the distance matrices of genetic markers $\{m_i\}_{i=1}^{N} \cup \{m_{new}\}$ and images $\{p_i\}_{i=1}^{N} \cup \{p_{new_k}\}$.

When large datasets are available for training, the matching task can also be addressed by a reduction to a binary classification problem, with one class representing matching pairs and the other non-matching pairs. This method is based on concatenating the genetic marker vector $m_i$ and the image vector $p_i$ to one vector $$\binom{m_i}{p_i}.$$

To avoid scaling issues, the two data sets are preprocessed separately by subtracting the mean vector value from each type of vectors, and dividing by the mean norm of the corresponding type across all training samples.

After the above normalization, each matching genotype/phenotype pair is concatenated to produce one vector of the matching type. Non-matching type vectors are generated by mixing between the genetic samples and the image samples.

A classifier, such as SVM classifier, is trained on a data set containing positive samples of matching pairs and negative samples of non-matching pairs.

During deployment, genetic marker vectors and image data vectors are normalized using the same procedure applied to the training data. The matching is chosen based on the classification score of the corresponding vectors:

$$\binom{m_{new}}{p_{new_1}}, \binom{m_{new}}{p_{new_2}}, \ldots, \binom{m_{new}}{p_{new_k}}.$$

Following the training phase, models for comparing genetic markers and visual data are obtained. In deployment a genetic marker $M_{new}$ and a set of face image (possible matches in the virtual line-up) $\{P_{new_1}, \ldots, P_{new_k}\}$ are provided. This genetic marker and those images are of personal unseen during training.

The input genetic marker and images are converted to vectors as before, using exactly the same process. e.g., for images, the faces are detected, the face regions are aligned, and descriptor vectors are extracted.

The matching scores between the vector of the genetic marker $m_{new}$ and the vectors of the face images $\{p_{new_1}, \ldots, p_{new_k}\}$ are then considered. This is done in accordance with the training algorithm used.

Scores for the NNT, inverse NNT algorithm and their generalized forms, as well as for the polygenetic tree methods PT1 and PT2 and for the binary classification method are explained above.

For CCA the system applies $W_X$ to $m_{new}$ and $W_Y$ to $\{p_{new_1}, \ldots, p_{new_k}\}$. The k matching scores are given by a distances function computed between the transformed genetic market and each of the transformed images. i.e., the selected image is the one which minimizes $$D(W_X^T m_{new}, W_Y^T p_{new_j}),$$

where $j=1 \ldots k$, and $D: R^l \times R^l \to R$ is a distance metric.

For Kernel CCA analog projections exist that map the input genetic and images samples to vectors in a common vector space.

Though a standard distance metric such as Euclidean distance can be used after the CCA or Kernel CCA transformation, it is sometimes beneficial to weigh the elements of the vectors by the corresponding correlation coefficients, as they vary for different locations in the target vectors.

If the i'th correlation coefficient (the correlation between the i-th coordinate of the mapped genes and images in the training set) is denoted by $\rho_i$, then for $u \in R^l$ the corresponding vector in correlation space $\hat{u}$ is defined by $\hat{u}_i = \rho_i u_i$.

The following six possible distance metrics are defined:

$$D_{L_1}(u, v) = \sum_{i=1}^{l} |u_i - v_i|$$

$$D_{CoL_1}(u, v) = \sum_{i=1}^{l} |\hat{u}_i - \hat{v}_i|$$

$$D_{L_2}(u, v) = \sum_{i=1}^{l} (u_i - v_i)^2$$

$$D_{CoL_2}(u, v) = \sum_{i=1}^{l} (\hat{u}_i - \hat{v}_i)^2$$

$$D_C(u, v) = 1 - \frac{u \cdot v}{\|u\| \|v\|}$$

$$D_{CC}(u, v) = 1 - \frac{\hat{u} \cdot \hat{v}}{\|\hat{u}\| \|\hat{v}\|}$$

By comparing matching accuracy over various datasets, it seems that the cosine distance in correlation space ($D_{CC}$) is preferable to the other distances.

The likelihood that none of the input images are matching is also learned. This is done by computing the statistics of the scores obtained for matching and non-matching pairs of genetic-markers and images not used during training (a validation dataset).

The scores obtained on the validation dataset are used to calibrate the scores obtained from the algorithms, i.e., to compute a mapping between the score values and the likelihood of correct matching. This is known as the classifier calibration problem, and previous solutions exist, e.g., for scores arising from Support Vector Machine Classification the system of [John C. Platt. Probabilistic outputs for support vector machines and comparisons to regularized likelihood methods. In Advances in Large Margin Classifiers, pages 61-74, 1999.].

The current system employs a simple binning method [Bianca Zadrozny and Charles Elkan. Learning and making decisions when costs and probabilities are both unknown. Proceedings of the seventh ACM SIGKDD international conference on Knowledge discovery and data mining, 2001.], in which the range of score values is divided into v=10 intervals, and the likelihood of having scores arising from matching or non-matching pairs is estimated in each bin (interval) by examining the ratio of matching and non-matching pairs that produce a score in that interval. In the case of multiple images in the virtual line-up, errors caused by multiple-hypothesis testing are controlled by employing False discovery rate (FDR) control [Yoav Benjamini and Yosef Hochberg. Controlling the false discovery rate: A practical and powerful approach to multiple testing. Journal of the Royal Statistical Society, 57, 1995.].

Figure 3:
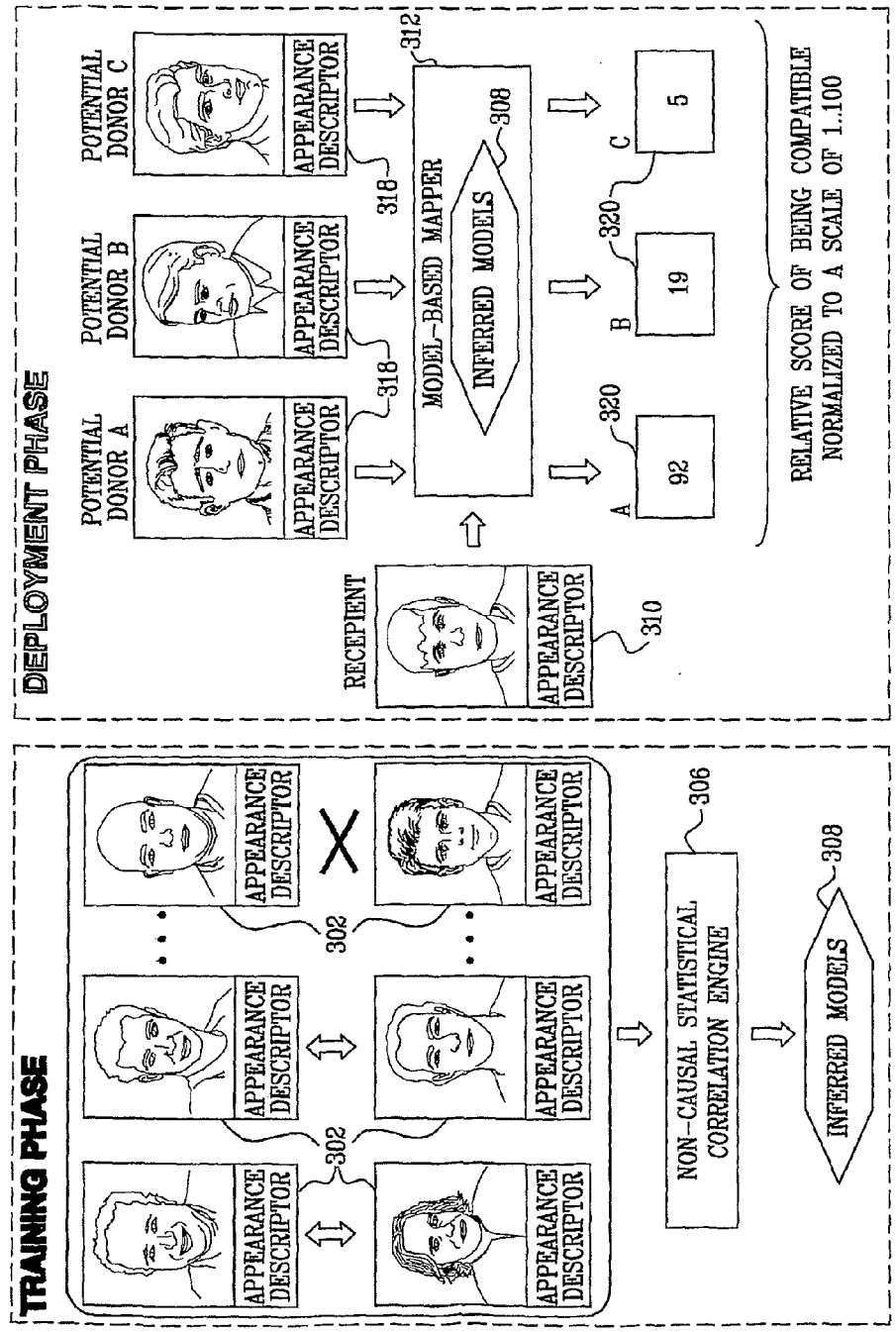
FIG. 3 is a simplified schematic illustration of a system and functionality for image-based non-invasive transplant compatibility screening based on inferring correlative, non-causal, statistical relationships between images of compatible persons in accordance with a preferred embodiment of the present invention.

Reference is now made to FIG. 3, which is a simplified schematic illustration of a system and functionality for image-based non-invasive transplant compatibility screening based on inferring non-causal (correlative) statistical relationships between images of compatible persons in accordance with a preferred embodiment of the present invention.

In accordance with a preferred embodiment of the present invention, image-based non-invasive transplant compatibility screening based on inferring non-causal (correlative) statistical relationships between images of compatible persons using genetic information includes statistical mapping functionality which collects a multiplicity of sets of facial image data 302 representing a multiplicity of pairs of individuals including many pairs of individuals who are known to be mutually transplant compatible and many pairs of individuals who are known to be mutually transplant incompatible. Preferably, image data on hundreds such compatible and incompatible pairs of individuals are employed in a training phase, more preferably thousands of such pairs of individuals and most preferably hundreds of thousands or millions of such pairs of individuals.

Preferably, the facial image data of each of the multiplicity of pairs of individuals is expressed or represented as a first multidimensional representation, such as a vector.

In accordance with a preferred embodiment of the present invention, a non-causal statistical correlation engine 306 is employed to infer correlative, non-causal, statistical relationships between the first multidimensional representations the transplant compatibility status of the respective pairs. Preferably, causal statistical relationships are excluded. Resulting inferred models 308 are stored by the system.

It is appreciated that the foregoing functionality may be considered to constitute a training phase which may be completed prior to deployment of the system for image-based non-invasive transplant compatibility screening or which may continue during the deployment phase of the functionality of the system.

In the deployment phase, these results of statistical mapping are preferably applied to facial image information, designated by reference numeral 310, from a prospective transplant recipient, not necessarily being an individual whose genetic information is used in the training phase, in a mapper 312 which uses the inferred models 308. It is a particular feature of the present invention that the prospective transplant recipient, whose facial image information 310 is mapped by mapper 312 need not be and normally is not one of the multiplicity of individuals whose genetic information is employed during the training phase.

Mapper 312 receives facial image data for a plurality of candidate transplant donors, collectively designated by reference numeral 318, and provides an output indicating which of the candidate donors have the greatest likelihood of being transplant compatible with the prospective transplant recipient, whose facial image information 310 is supplied to mapper 312 and thus selects the facial image of the most compatible potential donors from among the facial images of the plurality of candidate donors.

Preferably a likelihood score 320 is also provided. It is appreciated that the system and functionality of FIG. 3 provides a virtual transplant compatibility screening functionality.

In accordance with a preferred embodiment of the present invention, the multidimensional representations of facial image data are obtained by using one or more of the following methodologies:
  detection of a face region within the facial image data by using a learned template; and
  alignment of the face region by the detection of a set of fiducial points.

Generally stated, indicating the likelihood of donor-recipient transplant compatibility using facial images of potential donors and of a potential recipient preferably includes:
  representing facial image data of each of a multiplicity of the potential donors and of the potential recipient as multidimensional representations; and
  inferring correlative, non-causal, statistical relationships, indicative of transplant compatibility, between the multidimensional representations of the potential donors and the multidimensional representation of the potential recipient.

More particularly, estimating the likelihood of donor-recipient transplant compatibility using facial images of potential donors and of a potential recipient involves:
  collecting a multiplicity of facial image data pairs representing a multiplicity of pairs of individuals known to be transplant compatible or transplant incompatible;
  representing the facial image data of each of the multiplicity of individuals as pairs of multidimensional representations;
  inferring correlative, non-causal, statistical relationships between the pairs of multidimensional representations that indicate the likelihood of transplant compatibility of each associated pair of individuals; and
  employing correlative, non-causal, statistic relationships to estimate the likelihood of compatibility of multiple potential donors to a predetermined recipient, when the predetermined recipient and the multiple potential donors are represented by facial image data, wherein the multiple potential donors and the predetermined recipient are not necessarily among the multiplicity of pairs of individuals and normally are not among the multiplicity of pairs of individuals.

Preferably, the multiplicity of pairs of individuals known to be transplant compatible or transplant incompatible are identified by at least one of the following methods:
  determining Human Leukocyte Antigen (HLA) types by Serotyping;
  using Gene Sequencing of HLA genes to determine HLA compatibility;
  performing Sequence-Specific Primed PCR (PCR-SSP) HLA Typing; and
  estimating compatibility by means of recovering HLA Haplotypes.

In accordance with a preferred embodiment of the present invention, the multidimensional representation of the facial image data of each of the multiplicity of individuals includes at least one of the following representations:

a vector containing a multiplicity of histograms of image gradients at a multiplicity of image locations; and a vector containing a multiplicity of histograms of local-binary-patterns obtained at a multiplicity of image locations.

Preferably, the inferring of non-causal (correlative) statistical relationships employs Supervised Distance Metric Learning which is preferably applied to the vectors.

The importance of the embodiment of FIG. 3 may be appreciated by considering the following:

When Hematopoietic stem cells are transplanted into a patient, it is important to have good genetic compatibility between the recipient and the person from whom the cells are taken. Compatibility is currently assessed by HLA typing, which is both costly and requires taking a sample from each individual. Similarity in visual appearance increases the probability of genetic similarity, and two persons having genetic similarity are more likely to be compatible. The present invention is used to estimate the relevant genetic similarity based on facial images, hence providing an more affordable and accessible way to estimate increased chances of graft compatibility in humans.

The system and functionality preferably involves two stages. In a first (training) stage, pairs of face images of persons who are determined to be compatible to an acceptable degree are provided. In the second (deployment) stage, two facial images are given as input, and a matching score is provided.

In an illustrative example, the facial images of a recipient and of a potential donor are provided to the system. The system returns a predicted matching score. If the predicted matching score is above a certain threshold, the donor is referred for a biological test, such as HLA (Human leukocyte antigen) typing, which indicates compatibility with higher accuracy.

During the training stage unordered pairs of face images $\{P'_i, P''_i\}$, $i=1 \ldots N$ of persons who are known to be transplant-compatible are given as input. The compatibility of the matching pairs is determined by using tests such as HLA typing. In addition, incompatible images are provided, or are inferred by mixing among the input pairs.

The input face images are converted to a set of vectors $p_1'$, $p_1''$, $p_2'$, $p_2''$, ... as above. The faces are detected in each image, aligned, and then descriptors of several types are used to construct one vector per image.

Given the set of matching and non-matching pairs a distance function is constructed such that the distance between matching vectors is expected to be small, and the distance between non-matching vectors is expected to be high. This is known as the Supervised Distance Metric Learning problem, and existing solutions include Relevant Components Analysis [N. Shental, T. Hertz, D. Weinshall, and M. Pavel. Adjustment learning and relevant component analysis. In Proceedings of European Conference on Computer Vision, pages 776-790, 2002.], Kernel Regularized Relevant Component Analysis [E. Meyers and L. Wolf. Using biologically inspired features for face processing. International Journal of Computer Vision, 76(1):93-104, 2008.], and Discriminative Component Analysis [Steven C. H. Hoi, Wei Liu, Michael R. Lyu, and Wei-Ying Ma. Learning distance metrics with contextual constraints for image retrieval. Proceedings of IEEE Conference on Computer Vision and Pattern Recognition, New York, US, Jun. 17-22 2006.].

Following the training stage, a metric $D_T$ is obtained which given two face images $p_i$, $p_j$ returns a distance $D_T(p_i, p_j)$ which is related to the likelihood of donor-recipient compatibility between the persons photographed. The smaller the distance, the more likely the persons are to be compatible.

In order to convert the distance to a score function, a score calibration process is required. This process converts the output distance to a likelihood score. In the current system it is implemented using a binning technique as explained above.

Figure 4:
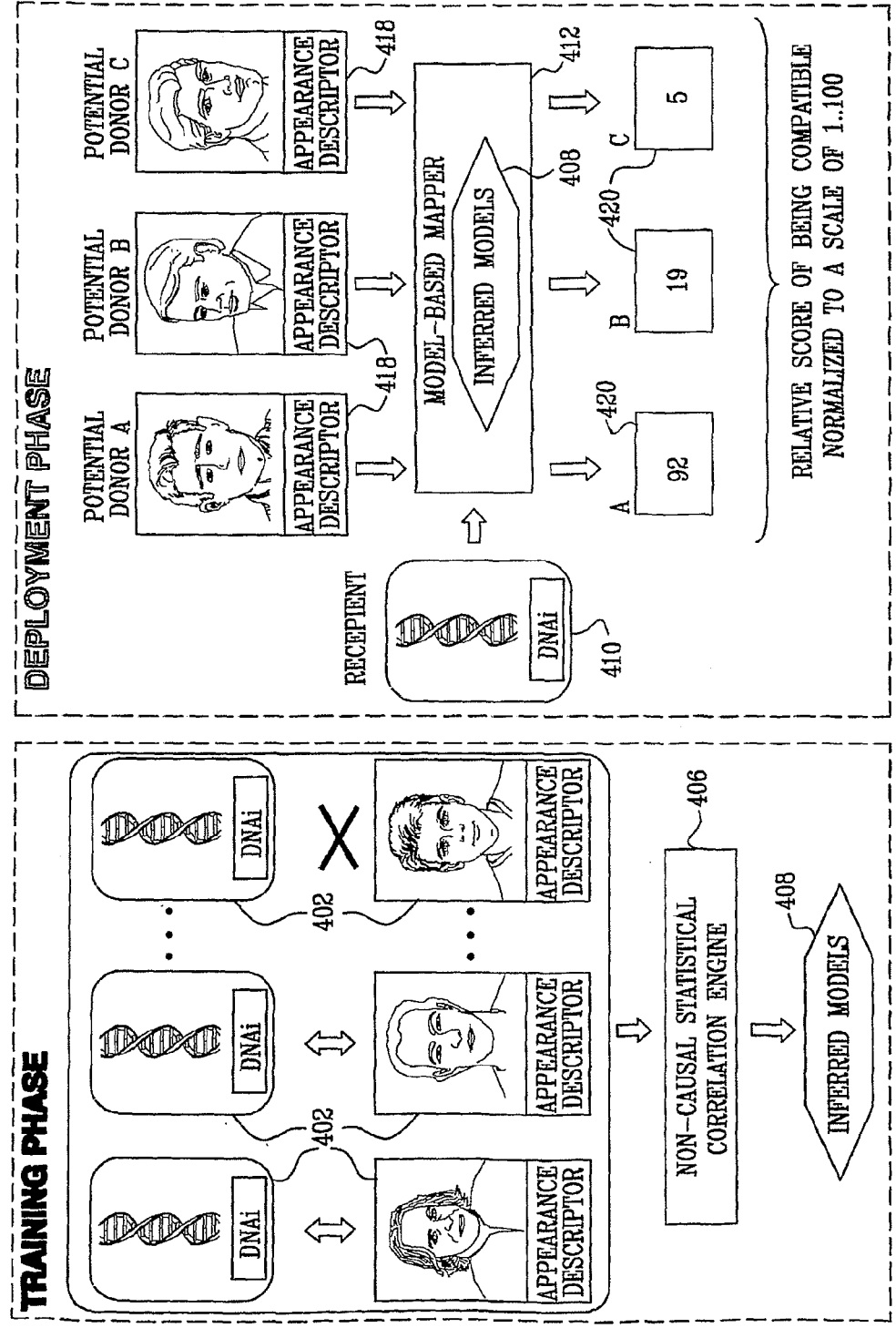
FIG. 4 is a simplified schematic illustration of a system and functionality for image-based and genetic information-based non-invasive transplant compatibility screening based on inferring correlative, non-causal, statistical relationships between images and genetic information in accordance with a preferred embodiment of the present invention.

Reference is now made to FIG. 4, which is a simplified schematic illustration of a system and functionality for image-based non-invasive transplant compatibility screening based on inferring correlative, non-causal, statistical relationships between images and genetic information in accordance with a preferred embodiment of the present invention.

In accordance with a preferred embodiment of the present invention, image-based non-invasive transplant compatibility screening based on inferring correlative, non-causal statistical relationships between images of compatible persons using genetic information includes statistical mapping functionality which collects a multiplicity of sets of genetic data and facial image data 402 representing a multiplicity of pairs of individuals including many pairs of individuals who are known to be mutually transplant compatible and many pairs of individuals who are known to be mutually transplant incompatible. Preferably sets of genetic data and facial image data on hundreds such compatible and incompatible pairs of individuals are employed in a training phase, more preferably thousands of such pairs of individuals and most preferably hundreds of thousands or millions of such pairs of individuals.

Preferably, the genetic information of one member of each of the multiplicity of pairs of individuals is expressed or represented as a first multidimensional representation, such as a vector and the facial image data of the other member of each of the multiplicity of pairs of individuals is expressed or represented as a second multidimensional representation, such as a vector.

In accordance with a preferred embodiment of the present invention, a non-causal statistical correlation engine 406 is employed to infer correlative, non-causal, statistical relationships between the first multidimensional representations and the second multidimensional representations. Resulting inferred models 408 are stored by the system.

It is appreciated that the foregoing functionality may be considered to constitute a training phase which may be completed prior to deployment of the system for image-based non-invasive transplant compatibility screening or which may continue during the deployment phase of the functionality of the system.

In the deployment phase, these results of statistical mapping are preferably applied to genetic information, designated by reference numeral 410, from a prospective transplant recipient, not necessarily being an individual whose genetic information is used in the training phase, in a mapper 412 which uses the inferred models 408. It is a particular feature of the present invention that the prospective transplant recipient, whose genetic information 410 is mapped by mapper 412, need not be and normally is not one of the multiplicity of individuals whose genetic information is employed during the training phase.

Mapper 412 receives facial image data for a plurality of candidate transplant donors, collectively designated by reference numeral 418, and provides an output indicating which of the candidate donors have the greatest likelihood of being transplant compatible with the prospective transplant recipient, whose genetic information 410 is supplied to mapper 412 and thus selects the facial image of the most compatible potential donors from among the facial images of the plurality of candidate donors.

Preferably a likelihood score 420 is also provided. It is appreciated that the system and functionality of FIG. 4 provides a virtual transplant compatibility screening functionality.

Generally stated, the likelihood of donor-recipient transplant compatibility is estimated using facial images of potential donors and genetic information of a potential recipient by providing results of statistical relationships between genetic information and facial image data produced by inferring correlative, non-causal, statistical relationships between first multidimensional representations of the genetic information and second multidimensional representations of the facial image data for a multiplicity of individuals, not necessarily including the potential recipient and the plurality of potential donors.

In accordance with a preferred embodiment of the present invention, the likelihood of donor-recipient transplant compatibility is indicated using facial images of potential donors and genetic information of a potential recipient by:

collecting information representing a multiplicity of pairs of individuals known to be transplant compatible or transplant incompatible, wherein the information includes genetic information regarding one individual of the pair and facial image data regarding the other individual of the pair;

representing the genetic information of each of the one individual of each pair of the multiplicity of pairs individuals and of the potential recipient as a first multidimensional representation;

representing the facial image data of each of the other individual of each pair of the multiplicity of pairs of individuals and of each of the potential donors as a second multidimensional representation;

providing results of statistical relationships between genetic information and facial image data produced by inferring correlative, non-causal, statistical relationships between first multidimensional representations of the genetic information and second multidimensional representations of the facial image data for a multiplicity of individuals, not necessarily including the potential recipient and the potential donors; and applying the results of the statistical relationships to genetic information obtained from the potential recipient and to the facial images of the potential donors, thereby to estimate the likelihood of donor-recipient transplant compatibility of each of the potential donors and the potential recipient.

In accordance with a preferred embodiment of the present invention, the first multidimensional representations are obtained by using one or more of the following methodologies:

representing nucleotide sequences of length n as vectors of length 4n wherein each element counts the number of occurrences of each nucleotide at a specific sequence location in the genetic information;

representing STR data of n loci as vectors of length 2n wherein each element depicts either the lower or the higher repetition number at one locus in the genetic information;

representing allele information of n loci, each having a multiplicity of $\gamma_i$, i=1 . . . n alleles as vectors of length $$\sum_{i=1}^{n} \gamma_i$$

wherein each vector element denotes the number of times each allele is present in the genetic information; and representing the genetic information implicitly by providing a similarity function between the genetic information arising from every two individuals.

Preferably, the second multidimensional representation employs at least one of the following algorithms:

detection of a face region within the facial image data by using a learned template; and alignment of the face region by the detection of a set of fiducial points, and the second multidimensional representation includes at least one of the following representations:

a vector containing a multiplicity of histograms of image gradients at a multiplicity of image locations; and a vector containing a multiplicity of histograms of local-binary-patterns obtained at a multiplicity of image locations.

In accordance with a preferred embodiment of the present invention, the providing results of statistical relationships employs at least one of the following algorithms:

Canonical Correlation Analysis;
Kernel Canonical Correlation Analysis;
Nearest Neighbor Transfer;
Generalized Nearest Neighbor Transfer;
Inverse Nearest Neighbor Transfer; and
Inverse Generalized Nearest Neighbor Transfer;
identification based on the structure of recovered phylogenetic-trees; and
statistical classifier learning of multidimensional representations each containing information from the first multidimensional representation and the second multidimensional representation.

Preferably, applying the results of the statistical relationships employs at least one of the following methods:

transformation of the facial image data and the genetic information using transformations obtained by employing Canonical Correlation Analysis;

transformation of the facial image data and the genetic information using transformations obtained by employing Kernel Canonical Correlation Analysis;

selection based on minimal $D_{L_1}$ distance;
selection based on minimal $D_{CoL_1}$ distance;
selection based on minimal $D_{L_2}$ distance;
selection based on minimal $D_{CoL_2}$ distance;
selection based on minimal $D_C$ distance;
selection based on minimal $D_{CC}$ distance;
selection based on the Nearest Neighbor Transfer decision rule;
selection based on the Generalized Nearest Neighbor Transfer decision rule;
selection based on the Inverse Nearest Neighbor Transfer decision rule;
selection based on the Inverse Generalized Nearest Neighbor Transfer decision rule;
selection based on examining the genetic information obtained from the potential recipient and the facial images of the potential donors within the context of phylogenetic trees constructed from the first multidimensional representations and the second multidimensional representations for the multiplicity of pairs; and selection based on applying classification rules to multidimensional representations each containing information from the first multidimensional representation obtained from the genetic information of the potential recipient and each of the second multidimensional representation obtained from the facial image data of the potential donors.

In accordance with a preferred embodiment of the present invention, the multiplicity of individuals known to be transplant compatible or transplant incompatible are identified by at least one of the following methods:
- examining human leukocyte antigen (HLA) types by Serotyping;
- using Gene Sequencing of HLA genes to determine HLA compatibility;
- performing Sequence-Specific Primed PCR (PCR-SSP) HLA Typing; and
- estimating compatibility by means of recovering HLA Haplotypes.

In the embodiment of FIG. 4, the genetic information of the recipient is available during the search for a compatible donor. This information can be used for the task of visual likelihood compatibility estimation.

The system is based on training and deployment stages. In the training stage, sets comprising of genetic markers from one person and facial image data from a transplant compatible person are provided. In the deployment stage, the genetic information of the recipient and a set of facial images are given as input, and a matching score is provided to each facial image. The genetic markers used are either those indicating transplant compatibility such as HLA typing or typing of other markers.

During the training stage sets of such genetic information and image information $\{M_i, P_i\}$, i=1 ... N arising from two persons who are known to transplant compatible are given as input. The compatibility of the matching pairs is determined by using tests such as HLA gene sequencing. In addition, incompatible images are provided, or are inferred by mixing among the input pairs.

It is appreciated that the form of this problem is computationally identical to the virtual line-up, i.e., in both cases one learns to match genetic information and facial images. The solution provided above to the virtual line-up applies here. Specifically, the input genetic markers and face images are converted to a set of vectors $m_1$, $m_2$, . . . , $m_N$ and $p_1$, $p_2$, . . . , $p_N$ as above. And any one of the algorithms proposed above, such as CCA and NNT can be used to learn correlations between the genetic data and the image data, and to evaluate matching scores during deployment.

Figure 5:
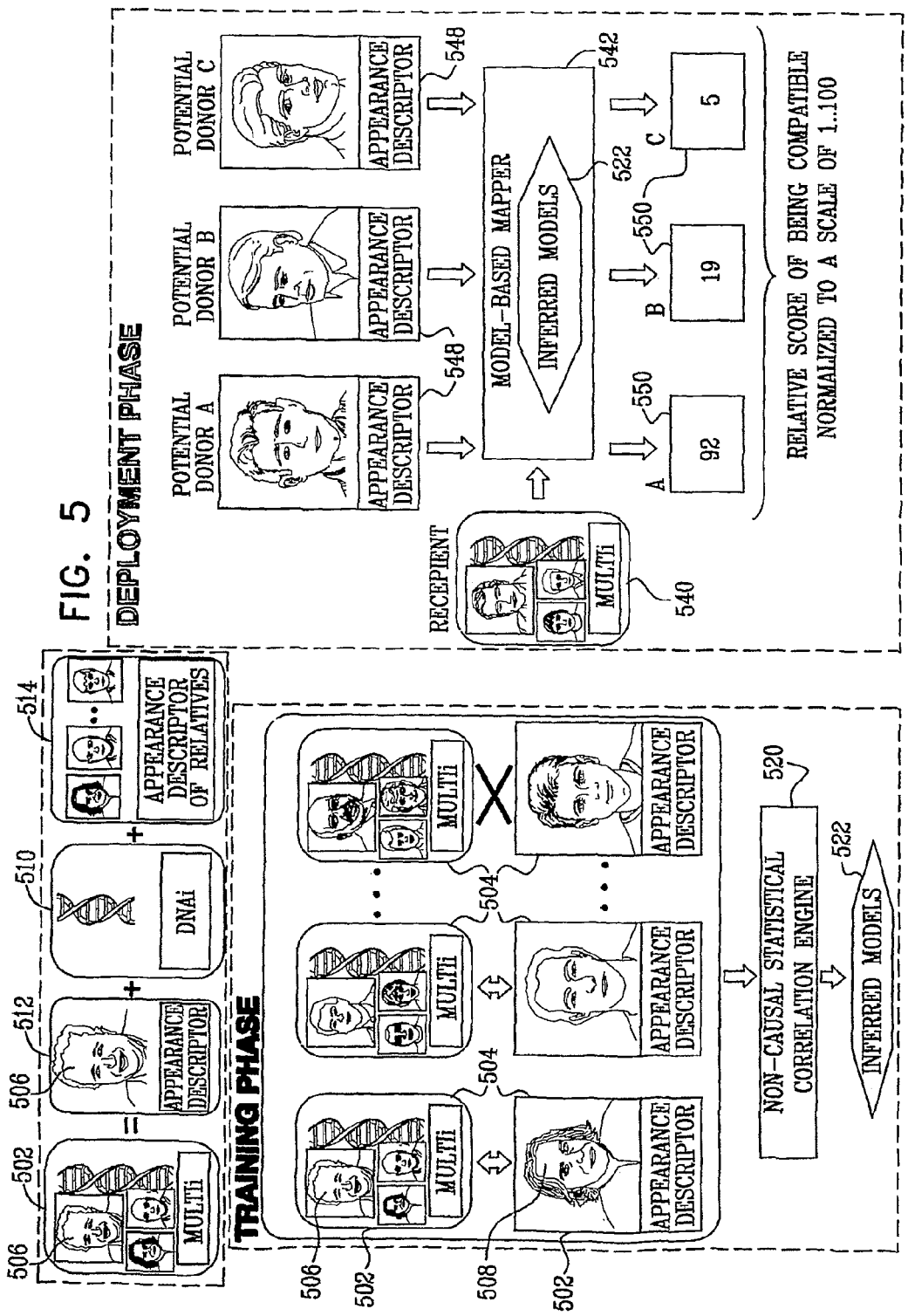
FIG. 5 is a simplified schematic illustration of a system and functionality for image-based and genetic information-based non-invasive transplant compatibility screening based on inferring correlative, non-causal, statistical relationships between images and genetic information in accordance with another preferred embodiment of the present invention.

Reference is now made to FIG. 5, which is a simplified schematic illustration of a system and functionality for image-based and genetic information-based non-invasive transplant compatibility screening based on inferring correlative, non-causal, statistical relationships between images and information of a multitude of types in accordance with a preferred embodiment of the present invention.

In accordance with a preferred embodiment of the present invention, there is provided image-based non-invasive transplant compatibility screening based on inferring correlative, non-causal, statistical relationships between images and genetic information of compatible persons. This embodiment employs statistical mapping functionality which collects a multiplicity of sets of genetic information and/or facial image data 502 representing a multiplicity of pairs 504 of individuals including many pairs of individuals who are known to be mutually transplant compatible and many pairs of individuals who are known to be mutually transplant incompatible. Preferably, genetic information and/or image data on hundreds of such compatible and incompatible pairs of individuals, more preferably thousands of such pairs of individuals and most preferably hundreds of thousands or millions of such pairs of individuals, is employed in a training phase.

In accordance with a preferred embodiment of the present invention, multiple types of information relating to one member, designated by reference numeral 506, of each of the multiplicity of pairs of individuals is expressed or represented as a set of multidimensional representations, such as a set of vectors, and the facial image data of the other member, designated by reference numeral 508, of each of the multiplicity of pairs of individuals is expressed or represented as a multidimensional representation, such as a vector.

Preferably, the multiple types of information relating to one member 506 of each of the multiplicity of pairs 504 of individuals include any number of the following:
- genetic information 510 of the member 506;
- facial image information 512 of the member 506; and
- facial image data 514 of the relatives of the member 506.

In accordance with a preferred embodiment of the present invention, a non-causal statistical correlation engine 520 is employed to infer correlative, non-causal, statistical relationships between the set of multidimensional representations obtained from the one member and the multidimensional representation obtained from the other member. Resulting inferred models 522 are stored by the system.

It is appreciated that the foregoing functionality may be considered to constitute a training phase which may be completed prior to deployment of the system for image-based non-invasive transplant compatibility screening or which may continue during the deployment phase of the functionality of the system.

In the deployment phase, these results of statistical mapping are preferably applied to information of a multitude of types, designated by reference numeral 540, relating to a prospective transplant recipient, not necessarily being an individual whose information is used in the training phase, in a mapper 542 which uses the inferred models 522. It is a particular feature of the present invention that the prospective transplant recipient, whose multiple types of information 540 are mapped by mapper 542, need not be and normally is not one of the multiplicity of individuals whose information of a multitude of types is employed during the training phase.

Mapper 542 receives facial image data for a plurality of candidate transplant donors, collectively designated by reference numeral 548, and provides an output indicating which of the candidate donors have the greatest likelihood of being transplant compatible with the prospective transplant recipient, whose information of a multitude of types 540 is supplied to mapper 542 and thus selects the facial image of the most compatible potential donors from among the facial images of the plurality of candidate donors.

Preferably a likelihood score 550 is also provided. It is appreciated that the system and functionality of FIG. 5 provides a virtual transplant compatibility screening functionality.

Generally stated, the likelihood of donor-recipient transplant compatibility is estimated using facial images of potential donors and information of a multitude of types of a potential recipient by providing results of statistical relationships between information of a multitude of types and facial image data produced by inferring correlative, non-causal, statistical relationships between a set of multidimensional representations of the information of a multitude of types and multidimensional representations of the facial image data for a multiplicity of individuals, not necessarily including the prospective recipient and the potential donors.

In accordance with a preferred embodiment of the present invention, the likelihood of donor-recipient transplant compatibility is indicated using facial images of potential donors and information of a multitude of types of a potential recipient by:
  collecting information representing a multiplicity of pairs of individuals known to be transplant compatible or transplant incompatible, wherein the information includes a multitude of information types regarding one individual of the pair and facial image data regarding the other individual of the pair;
  representing the genetic information included in the multitude of information types of each of the one individual of each pair of the multiplicity of pairs of individuals and of the potential recipient as a first type of multidimensional representation;
  representing the facial image data included in the multitude of information types of the one individual and of the potential recipient and of each of the other individual of each pair of the multiplicity of pairs of individuals and of each of the potential donors as a second type of multidimensional representation;
  providing results of statistical relationships between information of a multitude of types and facial image data produced by inferring correlative, non-causal, statistical relationships between multidimensional representations of the first and second type and multidimensional representations of the second type for a multiplicity of individuals, not necessarily including the potential recipient and the potential donors; and
  applying the results of the statistical relationships to information of a multitude of types obtained from the potential recipient and to the facial images of the potential donors, thereby to estimate the likelihood of donor-recipient transplant compatibility of each of the potential donors and the potential recipient.

In accordance with a preferred embodiment of the present invention, the multidimensional representations of the first type are obtained by using one or more of the following methodologies:
  representing nucleotide sequences of length n as vectors of length 4n wherein each element counts the number of occurrences of each nucleotide at a specific sequence location in the genetic information;
  representing STR data of n loci as vectors of length 2n wherein each element depicts either the lower or the higher repetition number at one locus in the genetic information;
  representing allele information of n loci, each having a multiplicity of $\gamma_i$, i=1 ... n alleles as vectors of length $$\sum_{i=1}^{n} \gamma_i$$

wherein each vector element denotes the number of times each allele is present in the genetic information; and
  representing the genetic information implicitly by providing a similarity function between the genetic information arising from every two individuals.

Preferably, the multidimensional representations of the second type employ at least one of the following algorithms:
  detection of a face region within the facial image data by using a learned template; and
  alignment of the face region by the detection of a set of fiducial points,
and the second type of multidimensional representation includes at least one of the following representations:
  a vector containing a multiplicity of histograms of image gradients at a multiplicity of image locations; and
  a vector containing a multiplicity of histograms of local-binary-patterns obtained at a multiplicity of image locations.

In accordance with a preferred embodiment of the present invention, the providing results of statistical relationships employs at least one of the following algorithms:
  Canonical Correlation Analysis;
  Kernel Canonical Correlation Analysis; and
  Nearest Neighbor Transfer;
  Generalized Nearest Neighbor Transfer;
  Inverse Nearest Neighbor Transfer; and
  Inverse Generalized Nearest Neighbor Transfer;
  identification based on the structure of recovered phylogenetic-trees;
  statistical classifier learning of multidimensional representations each containing information from the first multidimensional representation and the second multidimensional representation;
  Supervised Distance Metric Learning; and
  combining multiple statistical relationships employing supervised learning.

Preferably, applying the results of the statistical relationships employs at least one of the following methods:
  transformation of the facial image data and the genetic information using transformations obtained by employing Canonical Correlation Analysis;
  transformation of the facial image data and the genetic information using transformations obtained by employing Kernel Canonical Correlation Analysis;
  selection based on minimal $D_{L_1}$ distance;
  selection based on minimal $D_{CoL_1}$ distance;
  selection based on minimal $D_{L_2}$ distance;
  selection based on minimal $D_{CoL_2}$ distance;
  selection based on minimal $D_C$ distance;
  selection based on minimal $D_{CC}$ distance;
  selection based on the Nearest Neighbor Transfer decision rule;
  selection based on the Generalized Nearest Neighbor Transfer decision rule;
  selection based on the Inverse Nearest Neighbor Transfer decision rule;
  selection based on the Inverse Generalized Nearest Neighbor Transfer decision rule;
  selection based on examining the genetic information obtained from the potential recipient and the facial images of the potential donors within the context of phylogenetic trees constructed from the first multidimensional representations and the second multidimensional representations for the multiplicity of pairs;
  selection based on applying classification rules to multidimensional representations each containing information from the first multidimensional representation obtained from the genetic information of the potential recipient and each of the second multidimensional representation obtained from the facial image data of the potential donors;
  selection based on learned Distance Metrics; and
  selection based on combining multiple statistical relationships via a learned combination function.

In accordance with a preferred embodiment of the present invention, the multiplicity of individuals known to be transplant compatible or transplant incompatible are identified by at least one of the following methods:
- examining human leukocyte antigen (HLA) types by Serotyping;
- using Gene Sequencing of HLA genes to determine HLA compatibility;
- performing PCR-SSP HLA Typing; and
- estimating compatibility by means of recovering HLA Haplotypes.

In the embodiment of FIG. 5, various types of information obtained from the potential recipient are available during the search for a compatible donor. The types of information include genetic information, image information obtained from the recipient, and image information obtained from the relatives of the recipient. This information can be used for the task of visual likelihood compatibility estimation.

The system is based on training and deployment stages. In the training stage, sets comprising of information of a multitude of types from one person and facial image data from a transplant compatible person are provided. In the deployment stage, the information of a multitude of types of the recipient and a set of facial images are given as input, and a matching score is provided to each facial image. The genetic markers used are either those indicating transplant compatibility such as HLA typing or typing of other markers.

During the training stage sets of such information of a multitude of types and image information $\{S_i, P_i\}$, i=1 ... N arising from two persons who are known to transplant compatible are given as input. The compatibility of the matching pairs is determined by using tests such as HLA typing. In addition, incompatible images are provided, or are inferred by mixing among the input pairs.

Each set $S_i = \{M_i, P'_i, P_i^1, \ldots P_i^{J_i}\}$ is associated with one individual. It includes genetic information $M_i$ and facial image data $P_i$ of that individual, and face image data $P_i^1, \ldots P_i^{J_i}$ of $J_i$ relatives of that individual.

Preferably, three statistical models are learned and the combined. The first models transplant-compatibility dependent relationships between genetic data $M_i$ of one individual and facial image data of another $P_i$. The second models such relationships between face image data of one individual $P'_i$ and face image data of another $P_i$. The third models such relationships between face image data of the relatives of one individual $P_i^1, \ldots P_i^J$ and the facial image data of another $P_i$.

It is appreciated that the form of the first modeling is computationally identical to the virtual line-up, i.e., in both cases one learns to match genetic information and facial images. The solution provided above to the virtual line-up applies here. Specifically, the input genetic markers and face images are converted to a set of vectors $m_1, m_2, \ldots, m_N$ and $p_1, p_2, \ldots, p_N$ as above. And any one of the algorithms proposed above, such as CCA and NNT can be used to learn correlations between the genetic data and the image data, and to evaluate matching scores during deployment.

It is appreciated that the form of the second and third modeling is computationally identical to the transplant-compatibility testing based on facial images (as depicted in FIG. 3), as they also involve learning to match facial images based on supervised learning of match/no-match labels. The solution provided above to transplant-compatibility testing based on facial images. Specifically, the input face images are converted to a set of vectors and Supervised Distance Metric Learning is applied to learn distances that are small between vectors associated with images of compatible persons or to the relatives of compatible persons. The learned distance metric is then used, during deployment, to estimate transplant-compatibility.

Preferably, three separate models are learned from the training data, i.e., the training of the second and the third models are separated in spite of their similarity. Note that the second and the third models differ in the amount of information contained in each. Note also that for the third model, the number of relatives ($J_i$) vary. During training, each relative k provides one training pair ($P_i^k$, $P_i$). During deployment, results are averaged over all relatives of the potential recipient.

The training data is first divided into two parts, then the models are trained on the first part and evaluated on the second part. The results obtained on the second part are used to train a forth model which maps the output of each of the first three models onto a score measuring the likelihood of transplant compatibility, i.e., the output of the three models are converted to a vector which is classified by a forth classifier. This combination technique is known as stacking [D. H. Wolpert. Stacked generalization. Neural Networks, 5(2):241-259, 1992.]. In this embodiment it is employed by training a Support Vectors Machine on the output of the three learned models.

The foregoing description is based at least in part on the investigative work of the inventors described hereinbelow:

The appearance of an animal species is a complex phenotype partially encoded in its genome.

Previous work on linking genotype to visually-identifiable phenotypes has focused on univariate or low-dimensional traits such as eye color [R. A. Sturm and T. N. Frudakis. Eye colour: portals into pigmentation genes and ancestry. Trends in Genetics, 20(8):327-332, August 2004.], principal variations in skeletal structure [K. Chase, D. R. Carrier, F. R. Adler, T. Jarvik, E. A. Ostrander, T. D. Lorentzen, and K. G. Lark. Genetic basis for systems of skeletal quantitative traits: Principal component analysis of the canid skeleton. PNAS, 99:9930-9935, July 2002.] and height [N. B. Sutterm, et al. A single igf1 allele is a major determinant of small size in dogs. Science, 316(5821):112-115, April 2007.], as well as on the discovery of specific genes that contribute to these traits.

The present invention goes beyond single traits to the direct genotype-phenotype analysis of photographs and illustrations of animal species. It addresses the problems of (1) identification and (2) synthesis of images of previously unseen animals using genetic information. The present inventors demonstrate that both these problems are feasible: in a multiple choice test, algorithms presented hereinbelow identify with high accuracy the correct image of previously unseen humans, dogs, fish, birds and ants, based only on either variations in a short gene sequence or microsatellite data; additionally, using the same sequence images of unseen fish contours are approximated. The resulting predictions are based on correlative genotype-phenotype links rather than on specific gene targeting, and they employ microsatellite data and the cytochrome c oxidase I mitochondrial gene, both of which are assumed to have little causal influence on appearance. Such correlative links enable the use of high-dimensional phenotypes in genetic research, and applications may range from forensics to personalized medical treatment.

There is little doubt that appearance is to a large extent influenced by heritage, yet the actual mechanisms that determine people's looks may be difficult to unravel since they are likely to involve complex pathways consisting of a multitude of genes. This, however, does not eliminate the possibility of predicting appearance according to genetic data. In order to predict it is sufficient to discover statistical correlations between genetic markers and images, without having to describe the exact mechanism at work.

Moreover, correlations between genotype and phenotype can be identified even in the absence of direct causal relationship. The genes directly responsible for appearance are inherited together with other genes that are involved in completely different functions, thus generating many intricate interdependencies that can be exploited statistically. This distinction between function and correlation is demonstrated acutely in the experiments conducted, since microsatellites and a mitochondrial gene, which are unlikely to directly determine visual appearance, are employed.

The present invention applies learning the relations between genotype and phenotype to prediction of appearance based on genetic markers, i.e., using a training set $\{M_i, P_i\}_{i=1}^N$ of N matching markers and images, and a marker of a new organism $M_{new}$, to generate an image $\hat{P}_{new}$ such that $\hat{P}_{new}$ is a good approximation of the actual appearance of the organism.

One embodiment of the present invention identifies the image of an animal of the same species out of k candidate images $P_1, \ldots, P_k$ given its genotype M, where the genetic marker and the species in the candidate images are all previously unseen. It is appreciated that the ability to predict the image $\hat{P}$ that corresponds to the genetic marker M implies the ability to identify without difficulty the correct image as the one closest visually to $\hat{P}$. The converse is not true: the correlative nature of the learned genotype-phenotype relations can be used to solve the selection task without providing the ability to synthesize an image. Indeed, the inventors' experiments demonstrate that limited genetic data in the form of microsatellites or the COI gene provide sufficient information to allow correct identification at considerably higher success rates than the 1/k chance performance.

The experiments presented herein focus mainly on the task of multiple-choice identification of the correct image out of k candidate images, all previously unseen, to match a previously unseen genetic marker. Efforts directed to generating an image to match a previously unseen genetic marker are also described hereinbelow.

Throughout this work, linear models are used for prediction. First, both the genetic data (M) and the images (P) are represented as vectors m and p respectively, of lengths $n_m$ and $n_p$.

In the experiments two kinds of genetic data are principally employed: the mitochondrial gene cytochrome c oxidase I (COI) and microsatellites. Both are referred to as genetic markers.

Mitochondrial DNA (mtDNA) is normally inherited unchanged from the mother, with very limited recombination compared to nuclear DNA, yet its mutation rate is higher than that of nuclear DNA [W. M. Brown, M. George, and A. C. Wilson. Rapid evolution of animal mitochondrial DNA. PNAS, 76(4):1967-1971, April 1979.], resulting in low variance within species and high variance between different species, thus making it a promising candidate for species identification [J. C. Avise, et al. Intraspecific phylogeography: The mitochondrial DNA bridge between population genetics and systematics. Annual Review of Ecology and Systematics, 18:489-522, 1987.].

In addition, mtDNA contains very few introns and is easy to collect, which further increases its suitability for this purpose. In theory, many mitochondrial loci can be used; in practice, COI has been repeatedly employed for DNA barcoding and its discriminative effectiveness has been demonstrated in several species [P. D. N. Hebert, A. Cywinska, S. L. Ball, and J. R. deWaard. Biological identifications through DNA barcodes. Proceedings of The Royal Society Biological Sciences, 270(1512):313-321, February 2003; P. D. N. Hebert, S. Ratnasingham, and J. R. deWaard. Barcoding animal life: cytochrome c oxidase subunit 1 divergences among closely related species. Proceedings of the Royal Society B: Biological Sciences, 270:S96-S99, 2003.].

While the ability of COI to serve as a universal barcode has been doubted [K. W. Will and D. Rubinoff. Myth of the molecule: DNA barcodes for species cannot replace morphology for identification and classification. Cladistics, 20(1):47-55, 2004; T. R. Gregory. DNA barcoding does not compete with taxonomy. Nature, 434:1067, April 2005.], in this work COI sequence data is employed in many experiments, mainly due to the high availability of COI sequences for many species of the same genus, publicly available from the Barcode of Life Database (BOLD) [S. Ratnasingham and P. D. N. Hebert. bold: The barcode of life data system (http://www.barcodinglife.org). Molecular Ecology Notes, 7:355-364(10), May 2007.].

Microsatellite data is employed for identifying images of humans and dogs. Micro satellites are polymorphic short repeating sequences spread throughout the genome, and due to their high levels of polymorphism, they have been repeatedly used to establish evolutionary relationships [A. M. Bowcock, A. Ruiz-Linares, J. Tomfohrde, E. Minch, J. R. Kidd, and L. L. Cavalli-Sforza. High resolution of human evolutionary trees with polymorphic microsatellites. Nature, 368:455-457, March 1994.].

To describe COI sequences as vectors, the n nucleotides of each sequence (n is constant per dataset, and its value varies between 576 for ants and 669 for birds) as a vector of dimension $n_m$=4n of real numbers between 0 and 1. Each element marks the appearance of a specific nucleotide (A, G, C or T) at a specific location in the COI sequences of the species. In cases where there are multiple measurement in the BOLD database for a particular species, the elements mark the relative frequency of a nucleic acid of a certain type. It is appreciated that unlike the application to non mitochondrial sequences, there is only a maternal copy. In this representation, the dot product of two gene vectors is the expected number of agreements between the sequences. An alternative representation based on the Kimura two-parameter model (K2P) [M. Kimura. A simple method for estimating evolutionary rates of base substitutions through comparative studies of nucleotide sequences. J Mol Evol, 16(2):111-120, December 1980.], which allows different probabilities for different kinds of nucleotide substitutions (transitions and transversions), was also tested, with nearly identical results.

The representation of microsatellite data is similar, where each locus with l different repetition lengths, i.e., l different alleles, is associated with l locations in the feature vector, and a value of 1 is assigned to the vector location associated with the repetition length of the current sample. For humans there is one sample per person. For the dog breed dataset, it may happen that there are several microsatellites per one breed, and the values are averaged between the different individuals of the same breed.

The visual data in our animal experiments comprises animal species images or dog breed images collected from various sources. Each image is represented as a single vector, which is obtained using a modern image representation method.

During the last few years, considerable progress has been made in the development of efficient visual representations serving as the core of several accurate computer vision systems. For example, real-time systems now exist that can detect specific classes of objects, such as people and cars, within complex images.

Often, an image is represented by a set of high-dimensional feature vectors, which describe its appearance at various locations. Among the most popular is the SIFT descriptor [D. G. Lowe. Distinctive image features from scale-invariant keypoints. International Journal of Computer Vision, 60(2):91-110, November 2004.], which captures the distribution of local image-edge orientations and is designed to be invariant to scaling and rigid image-transforms and is almost unaffected by local appearance perturbations.

One paradigm that has been proven effective despite its simplicity is the "bag-of-features" paradigm [T. Leung and J. Malik. Representing and recognizing the visual appearance of materials using three-dimensional textons. International Journal of Computer Vision, 43(1):29-44, 2001; R. Fergus, P. Perona, and A. Zisserman. Object class recognition by unsupervised scale-invariant learning. In Proceedings 2003 IEEE Computer Society Conference on Computer Vision and Pattern Recognition, volume 2, pages II-264-II-271, 2003]. In this paradigm, image descriptors from each training image are extracted at visually distinct or, alternatively, at random image locations. Next, the vector space of image descriptors is partitioned by employing a clustering algorithm of all descriptors arising from the training images. Each image (training or new) is then represented by the number of descriptors extracted from it which belong to each partition of the vector space.

For the representation of images as vectors primarily a bag-of-SIFT-features representation is employed. The visual descriptors of the images are computed by the bag-of-sift implementation of Andrea Vendaldi available at http://vision.ucla.edu/vedaldi/code/bag/bag.html. This implementation uses hierarchical K-means [D. Nister and H. Stewenius. Scalable recognition with a vocabulary tree. In Proceedings of the 2006 IEEE Computer Society Conference on Computer Vision and Pattern Recognition, pages 2161-2168, 2006.] for partitioning the descriptor space. Keypoints are selected at random locations [E. Nowak, F. Jurie, and B. Triggs. Sampling strategies for bag-of-features image classification. In European Conference on Computer Vision. Springer, 2006.]. Note that the dictionary for this representation was recomputed at each run in order to avoid the use of testing data in the training stage. For all data sets $n_p \approx 11,111$.

Other paradigms for visual recognition include the hierarchical neuroscience-motivated systems [Y. LeCun, L. Bottou, Y. Bengio, and P. Haffner. Gradient-based learning applied to document recognition. Proceedings of the IEEE, 86(11): 2278-2324, November 1998, M. Riesenhuber and T. Poggio. Hierarchical models of object recognition in cortex. Nature Neuroscience, 2(11):1019-1025, 1999.]. These systems are designed to have a layered structure, in which invariance and selectivity are increased toward the top of the hierarchy. Experiments have also been conducted with the system of $C_1$ descriptors [T. Serre, L. Wolf, S. Bileschi, M. Riesenhuber, and T. Poggio. Robust object recognition with cortex-like mechanisms. IEEE Trans Pattern Anal Mach Intell, 29(3): 411-426, 2007.] that show a performance level similar to that of the bag-of-features paradigm.

Five data sets are employed: Fishes of Australia [R. D. Ward, T. S. Zemlak, B. H. Innes, P. R. Last, and P. D. N. Hebert. DNA barcoding Australia's fish species. Philosophical Transactions of The Royal Society Biological Sciences, 360(1462):1847-1857, October 2005.], Ant Diversity in Northern Madagascar [M. A. Smith, B. L. Fisher, and P. D. N. Hebert. DNA barcoding for effective biodiversity assessment of a hyperdiverse arthropod group: the ants of Madagascar. Philosophical Trans. of The Royal Soc. Biological Sciences, 360(1462):1825-1834, October 2005.], Birds of North America—Phase II project [K. C. Kerr, M. Y. Stoeckle, C. J. Dove, L. A. Weigt, C. M. Francis, and P. D. Hebert. Comprehensive DNA barcode coverage of North American birds. Molecular Ecology Notes, 7(4):535-543, July 2007.], Purebred Domestic Dogs [H. G. Parker, L. V. Kim, N. B. Sutter, S. Carlson, T. D. L., T. B. Malek, G. S. Johnson, H. B. DeFrance, E. A. Ostrander, and L. Kruglyak. Genetic Structure of the Purebred Domestic Dog. Science, 304(5674):1160-1164, 2004], and a new human dataset. All COI sequences were retrieved from BOLD, and the microsatellite data of Parker et al. [H. G. Parker, L. V. Kim, N. B. Sutter, S. Carlson, T. D. L., T. B. Malek, G. S. Johnson, H. B. DeFrance, E. A. Ostrander, and L. Kruglyak. Genetic Structure of the Purebred Domestic Dog. Science, 304(5674):1160-1164, 2004 was used.

By locating matching images four data sets were constructed, containing multiple genotype-phenotype pairs (M, P), where M stands for the genetic data (COI gene sequences for the first three data sets, and microsatellite data for the fourth and fifth) and P is a single image of an animal of that species. No human, dog breed, fish or ant species is associated with more than one image, while the bird data set contains several genetic markers and images for each species.

The Barcode of Life Database contains 192 unique species in the Fishes of Australia project. Fish images were retrieved from FishBase (http://filaman.ifm-geomar.de/home.htm). Reasonable illustrations for 157 out of the 192 species were found. Note that the illustrations vary in style and quality.

Ant images were retrieved from AntWeb (http://www.antweb.org/). Out of 86 ant species sequenced in the Ant Diversity in Northern Madagascar Barcode of Life project, 26 entries were matched with images in the AntWeb site. For each ant there are three photographs: head, profile and dorsal. The fish and ant images were matched to the BOLD record by the species name.

Bird sequences and images were taken from the Birds of North America—Phase II project at Barcode of Life Database [K. C. Kerr, M. Y. Stoeckle, C. J. Dove, L. A. Weigt, C. M. Francis, and P. D. Hebert. Comprehensive DNA barcode coverage of North American birds. Molecular Ecology Notes, 7(4):535-543, July 2007.] itself. Out of 657 unique bird species with sequences, only 25 have images depicting the wing of the dead bird. Several sequences and images are available for each species, spanning a total of 125 sequences and matching images. Those images were flipped such that all bird wings would point left, and cropped them such that all the paper signs which were visible in the original images were removed.

The dogs included in the experiments are domestic breeds and images were collected from various online locations by web searches. Overall, images of dogs belonging to 60 different breeds were collected. All 157 fish images are available from http://www.cs.tau.ac.il/~wolf/phenotype/fish/all-fish.html, the disclosure of which is hereby incorporated by reference. Bird wing images are available from http://www.cs.tau.ac.il/~wolf/phenotype/wing/wings.html, and ant images are available from the following URLs: http://www.cs.tau.ac.il/~wolf/phenotype/ants_head/ants_head.html for head view, http://www.cs.tau.ac.il/~wolf/phenotype/ants_dorsal/ants_dorsal.html for dorsal view and http://www.cs.tau.ac.il/~wolf/phenotype/ants_profile/ants_profile.html for profile view. The disclosure of the aforementioned web sites are hereby incorporated by reference.

A dataset containing STRs obtained from 10 loci in the human genome and human face images was collected. The dataset contains genetic information and images from 126 male adults aged between 25 and 40. One image per human subject was used.

The images were taken at various indoor or outdoor locations and vary in quality. They present a variety of illumination conditions, head poses, face region resolution and facial expression.

The face region in each image was automatically detected and aligned as explained above. Each image was then represented by using histograms of image gradients, and by using histograms of local binary patterns, as explained above.

The problem to be solved was formulated as follows:

Given a training set $\{m_i, p_i\}_{i=1}^n$ of n matching genetic markers and images, a marker of a new organism $m_{new}$ and a set of images of unseen species $\{p_{new_1}, \ldots, p_{new_k}\}$ choose the image which best matches the new marker. In most of the experiments, k=2.

The most direct approach to solving forced matching tests is to learn the joint probability Pr(m, p) and choose the image $p_{new_i}$ that maximizes $Pr(m_{new}, p_{new_i})$. Learning this joint probability distribution, however, is difficult and may not be necessary. During experimentation, several method presented hereinabove in the description of the embodiment of FIG. 2 are used.

CCA minimizes the distances between matching genes and images, while disregarding the distances between non-matching genes and images. An alternative optimization goal for learning the two transformations $W_X$ and $W_Y$ combines the minimization of distances between matching pairs with the maximization of distances between non-matching pairs, thus attempting to achieve maximal discriminative ability. This approach has been developed in [Dahua Lin and Xiaoou Tang. Inter-modality face recognition. Proceedings of 9th IEEE European Conference on Computer Vision (ECCV 2006), pages 13-26, 2006.] for the general case where the samples come from several classes. It is referred to as Common Discriminant Feature Extraction (CDFE). It is adopted here for the forced matching cased, where there are only matching and non-matching pairs. Denote by $x_i$ the centered versions of the matching genetic marker vectors $m_i$, i.e., the vectors obtained after subtracting the mean vector value computed over all genetic markers in the training set. Denote by $y_i$ the analog centered versions of the visual phenotype vectors $p_i$. The distances between matching pairs and the distances between non-matching pairs are, respectively:

$$\frac{1}{n}\sum_{i=1}^n \|W_X^T x_i - W_Y^T y_i\|^2,$$

$$\frac{1}{n(n-1)}\sum_{1 \le i \ne j \le n} \|W_X^T x_i - W_Y^T y_j\|^2$$

Regularization is accomplished by including additional terms representing the local consistencies:

$$\frac{1}{n}\sum_{i=1}^n \sum_{j=1}^n \omega_{ij}^M \|W_X^T x_i - W_X^T x_j\|^2,$$

$$\omega_{ij}^M = \exp\left(-\frac{\|x_i - x_j\|^2}{\sigma_M^2}\right)$$

and similarly for y. Two parameters, α and β represent the trade-off between matching distances, non-matching distances and local consistency.

The algorithm has not been applied by in [Dahua Lin and Xiaoou Tang. Inter-modality face recognition. Proceedings of 9th IEEE European Conference on Computer Vision (ECCV 2006), pages 13-26, 2006.] to the match/no-match problem, where each class contains a single gene/image pair. The experiments show considerably better performance using ridge-like regularization instead of local consistency, so the algorithm has been modified to use ridge regularization. Therefore, the parameters are α, the trade-off between the terms for the matching pairs and non-matching pairs, and η, the standard ridge regularization parameter, employed as before.

The Maximal Margin Robot (MMR) method [Tijl De Bie Sandor Szedmak and David Hardoon. A metamorphosis of canonical correlation analysis into multivariate maximum margin learning. Proc. of the 15th European Symposium on Artificial Neural Networks (ESANN 2007), April 2007.] transforms the CCA formalization to a maximal-margin problem, and the corresponding solution can be seen as a generalization of Support Vector Machines for the case where both inputs and outputs are vectors. Rather than maximizing the sum of correlations, MMR maximizes the minimal correlation. Robustness to outliers is maintained through the inclusion of slack variables. This formalization produces the following quadratic programming problem:

$$\min_{W,\xi} \frac{1}{2}\|W\|_F^2 + C1^T\xi, \text{ subject to}$$

$$\forall \ 1 \le i \le n$$

$$y_i^T W x_i \ge 1 - \xi_i$$

$$\xi_i \ge 0$$

As a matching score between a genotype $x_{new}$ and a phenotype $y_{new_k}$, $y_{new_k}^T W x_{new}$ is used.

The MMR method considers the minimal correlation as the margin. In an alternative formulation, is termed Preference Margin Optimization (PMO), the margin is defined as the difference between the correlation of matching pairs and the correlation of non-matching pairs. This is similar to Support Vector Machines (SVMs), in which margins measure separation between classes.

The problem is formulated as the following QP problem:

$$\min_{W,\xi} \frac{1}{2}\|W\|_F^2 + \frac{C}{n}1^T\xi, \text{ subject to:}$$

$$\forall \ i \ne j$$

$$\xi_{ij} \ge 0,$$

$$y_i^T W x_i - y_j^T W x_i \ge 1 - \xi_{ij}$$

As a matching score between a genotype $x_{new}$ and a phenotype $y_{new_k}$, $y_{new_k}^T W x_{new}$ is used in the PMO method.

Since using all available constraints results in a possibly large number of constraints (n(n−1)), a partial subset of constraints is chosen. Using r constraints for each genetic marker in the training set, these r constraints are chosen by first performing Canonical Correlation Analysis on the training set, and then choosing the r phenotype vectors that are best correlated with the genetic marker to serve as constraints. While the choice of r can potentially affect performance significantly, empirical tests show that increasing r above 20 does not result in further improvements.

The experimental results presented in this work are evaluated using holdout-type cross validation: in each of the trials of an experiment, 90% of the data were chosen randomly to be used as training set, and the remaining 10% were used as test set. When comparing the influence of various parameters on the results of the same data set, care was taken to use the same divisions to training and test data in each experiment. When using the bird wings data set, no single species appears in both the training and test sets. In the identification experiments, for each genetic marker in the test set, an experiment is performed for each combination of the true image and another test image, and the results are averaged over all pairs. 100 trials were used with the above procedure.

In the following presentation of results, mean and standard deviation of identification accuracy is indicated across all trials for all data sets for k=2 (one matching image and one non-matching image), using linear regularized CCA with $\eta=0.05$, with the main genetic and image representations, compared with the Nearest Neighbor Transfer method. For humans, the NNT method was replaced with the Inverse Nearest Neighbor Transfer (INNT) method due to the limited nature of the genetic information used. Conversely it is believed that INNT is not effective for the less specialized image representation of the four animal datasets.

TABLE 1

Mean ± standard deviation identification accuracy (percent), using linear regularized CCA with $\eta = 0.05$, compared with Nearest Neighbor Transfer. Results are for forced choice with and k = 2.

| Data set | Number of samples | % correct identification CCA | NNT/INNT |
|---|---|---|---|
| Fish | 157 | 90.5 ± 4.0 | 68.6 ± 5.6 |
| Bird wings | 25 | 72.0 ± 13.7 | 53.8 ± 9.9 |
| Ants (profile view) | 26 | 63.8 ± 21.3 | 53.8 ± 10.8 |
| Ants (head view) | 26 | 55.8 ± 20.3 | 54.2 ± 12.3 |
| Ants (dorsal view) | 26 | 59.3 ± 19.9 | 54.6 ± 8.7 |
| Dogs | 60 | 63.9 ± 13.0 | 53.3 ± 6.8 |
| Humans | 126 | 58.7 ± 9.6 | 63.6 ± 10.5 |

Table 1 shows the identification results for the fish, bird-wing, ant, dog, and human data sets using the default settings: forced selection out of two options (k=2), genetic markers representing nucleotide or allele frequency, and images represented using bag-of-SIFT (animals) or the above-mentioned face descriptor for humans.

The results demonstrate that image identification based on genetic markers is possible. It is also evident that CCA performs better than NNT in most datasets, but not for humans, where INNT outperforms it.

The varying performance level can be partly accounted for by the training set sizes (when using as many training images in the fish experiments as in the ant experiments, performance drops to 77%), and variations in the quality of the genetic markers and images. The images in the dog data set were collected from a large number of websites using web searches and thus lack standard lighting and pose, and at times include multiple irrelevant background details, while at the other extreme, the bird wing images are standardized, thus explaining the higher accuracy despite the lower number of samples. Performance differences may also be partially explained by the different nature of the genetic markers (COI sequences for fish, birds and ants vs. microsatellites for dogs and humans).

Figure 6:
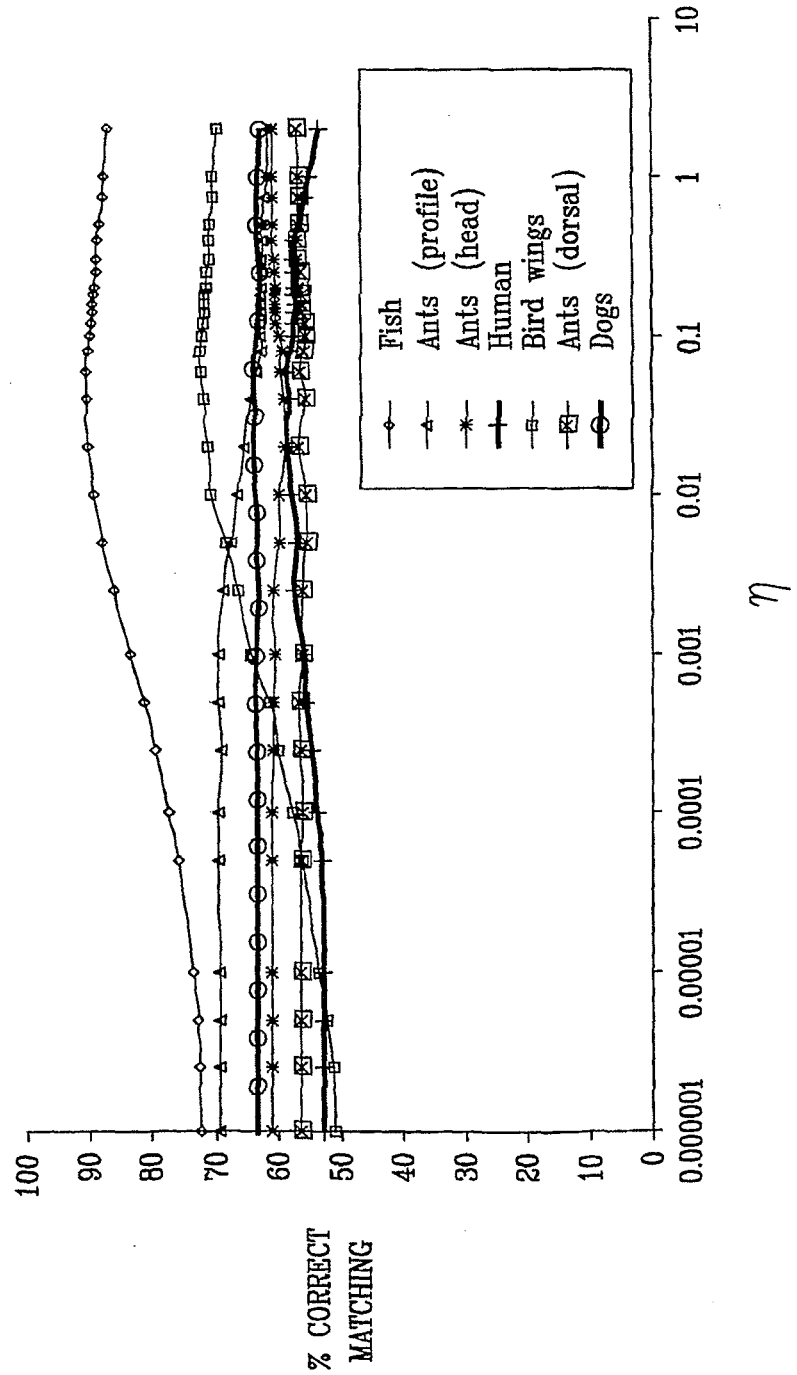
FIG. 6 is a graph depicting experimental results studying the effects of changing the regularization parameter of Canonical Correlation Analysis on Canonical Correlation Analysis based identification accuracy.

The influence of $\eta$, the parameter controlling ridge regularization for CCA, is initially examined. FIG. 6 shows results for varying values of $\eta$. As can be seen, the performance level is stable across a large range of the regularization parameter, and the value is set to 0.05 for all further experiments.

$\tau$ is the parameter controlling Gaussian kernel width, and FIG. 7A shows how KCCA matching accuracy varies when $\tau$ is changed. For comparisons to other methods described hereinbelow a fixed value of $\tau=0.25$ is used.

The CDFE $\alpha$ parameter controls the trade-off between matching pairs distances and non-matching pairs distances. FIG. 7B shows CDFE matching results using various values of $\alpha$, with $\eta=0.05$. For comparison, described hereinbelow, between the algorithms, $\alpha=2$.

It can be seen from FIGS. 6 and 7A-7B that matching accuracy remains stable across a wide range of parameter choices. The results would change little if other parameters are used. This is also true with regard to the influence of C, the trade-off parameter between margin and slack, in the maximal-margin methods (MMR, PMO, and SVM). Their performance was found to be nearly identical over a very wide range of C values, and C=1 was used for all experiments described hereinbelow.

Table 2 shows a comparison between the matching algorithms on the fish, bird wing, all ant data sets, dogs and humans. It can be seen that regularized linear CCA achieves best performance on nearly all data sets. The correlation-based variants are close behind, and the non-correlation-based methods (SVM, NNT, PT1, PT2) are far behind, except for humans.

The results also suggest that the reduction to a binary classification problem may not be suitable. A possible reason may be the impoverished nature of this representation, which projects all the data to just one dimension. Another reason may be that non-matches that are "almost-matches" do not affect training of correlation methods much (or at all, depending on the method), while they can harm the training of a binary classifier considerably.

TABLE 2

Matching accuracy (% and standard deviation) on the fish, bird wing and all ant data sets using all algorithms: Regularized Canonical Correlation Analysis (CCA), Kernel Canonical Correlation Analysis (KCCA), Common Discriminant Feature Extraction (CDFE); Maximal Margin Robot (MMR), Preference Margin Optimization (PMO), Binarization using Support Vector Machine (SVM), Nearest Neighbor Transfer (NNT), inverse Nearest Neighbor Transfer (INNT), Phylogenetic Tree distance (PT1), Phylogenetic Tree similarity (PT2).

| Algo-Rithm | Fish | Wing | Ants profile | Ants head | Ants dorsal | Dogs | Humans |
|---|---|---|---|---|---|---|---|
| CCA | 90.5 ± 4 | 72.0 ± 14 | 63.8 ± 21 | 55.8 ± 20 | 59.3 ± 20 | 63.9 ± 13 | 58.7 ± 10 |
| KCCA | 87.1 ± 5 | 61.8 ± 14 | 64.2 ± 20 | 58.5 ± 20 | 57.5 ± 18 | | 52.7 ± 11 |
| CDFE | 85.8 ± 6 | 67.5 ± 15 | 60.2 ± 23 | 58.0 ± 22 | 54.7 ± 24 | | |
| MMR | 86.2 ± 5 | 69.6 ± 14 | 61.7 ± 23 | 56.2 ± 20 | 55.5 ± 23 | | |
| PMO | 86.8 ± 6 | 68.5 ± 15 | 60.3 ± 24 | 58.5 ± 18 | 54.2 ± 22 | | |

TABLE 2-continued

Matching accuracy (% and standard deviation) on the fish, bird wing and all ant data sets using all algorithms: Regularized Canonical Correlation Analysis (CCA), Kernel Canonical Correlation Analysis (KCCA), Common Discriminant Feature Extraction (CDFE); Maximal Margin Robot (MMR), Preference Margin Optimization (PMO), Binarization using Support Vector Machine (SVM), Nearest Neighbor Transfer (NNT), inverse Nearest Neighbor Transfer (INNT), Phylogenetic Tree distance (PT1), Phylogenetic Tree similarity (PT2).

| Algo-Rithm | Fish | Wing | Ants profile | Ants head | Ants dorsal | Dogs | Humans |
|---|---|---|---|---|---|---|---|
| SVM | 57.6 ± 3 | 53.0 ± 5 | 56.8 ± 17 | 54.7 ± 16 | 54.8 ± 17 | | 50.17 ± 11 |
| NNT | 68.6 ± 6 | 53.8 ± 10 | 53.8 ± 10 | 54.2 ± 12 | 51.6 ± 9 | 53.3 ± 7 | 54.9 ± 10 |
| INNT | | | | | | | 63.6 ± 11 |
| PT1 | 77.6 ± 7 | 63.2 ± 16 | 57.2 ± 16 | 50.0 ± 21 | 61.8 ± 22 | | |
| PT2 | 64.1 ± 6 | 57.9 ± 14 | 47.1 ± 23 | 44.2 ± 21 | 50.9 ± 23 | | 50.6 ± 11 |

In the representation used for the experiments described herein, the similarity between two gene sequences is the number of agreements between the sequences. An alternative representation in which different probabilities are used for transitions and transversions as in the Kimura two-parameter model [M. Kimura. A simple method for estimating evolutionary rates of base substitutions through comparative studies of nucleotide sequences. J Mol Evol, 16(2):111-120, December 1980.], was tested as well. The results obtained are very similar to the baseline similarity. The K2P model parameters used were $\alpha=0.1$ (probability of transitions), $\beta=0.05$ (probability of transversions). Other choices of parameters yielded very similar, or worse, results.

A distance metric is required to choose the more similar pair of vectors after transformation. Several distance metrics are compared for matching with CCA ($\eta=0.05$). Table 3 shows a comparison that was performed on the fish dataset, between the distance metrics that are described hereinabove with reference to the embodiment of FIG. 2.

TABLE 3

Matching accuracy (% and standard deviation) for fish using CCA with different distance metrics.

| Metric | % Accuracy | Metric | % | Metric | % |
|---|---|---|---|---|---|
| $L_1$ | 75.2 ± 5.8 | $CoL_1$ | 85.1 ± 4.8 | C | 73.1 ± 7.9 |
| $L_2$ | 71.1 ± 7.3 | $CoL_2$ | 89.3 ± 4.2 | CC | 90.5 ± 4.1 |

Figure 8:
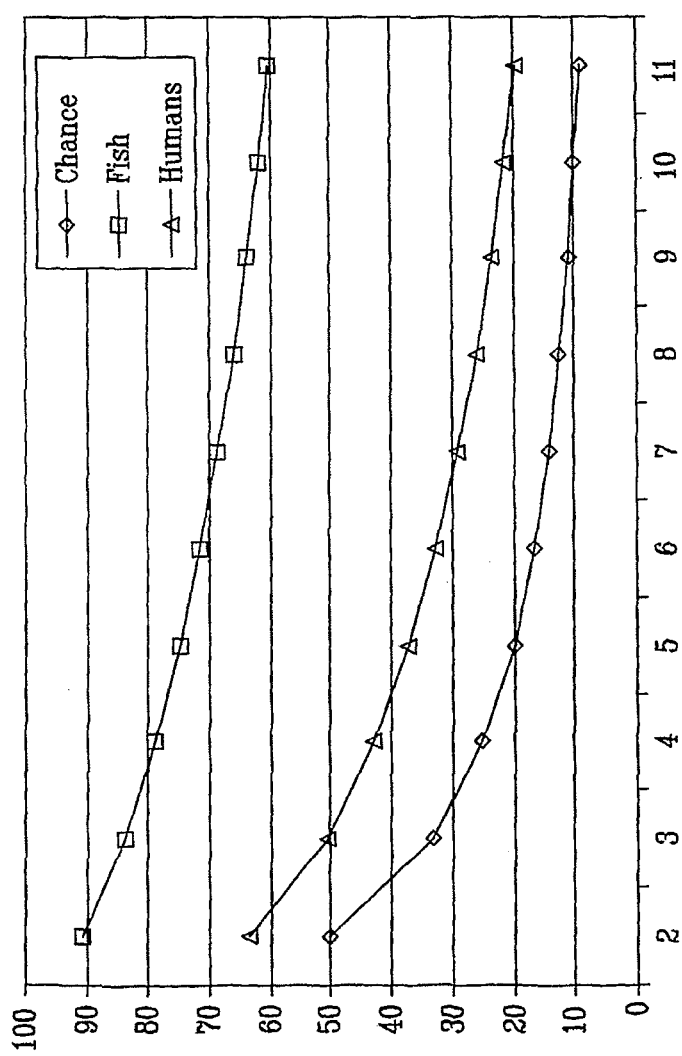
FIG. 8 is a graph depicting success rate for forced-matching tests, while varying the number of possible choices from 2 to 11, in which results are reported for fish using the Canonical Correlation Analysis method with a regularization factor of 0.05 and for humans with the Inverse Nearest Neighbor Transform method and the chance success rate is also shown.

Experiments that show the effect of varying the number of choices (k) in the forced-matching tests have also been conducted. As can be seen in FIG. 8, for the fish and human datasets, the matching score decreases gradually as k increases, while maintaining the same pattern.

For the bird data-set, several genetic markers and images from members of the same species are available, which enables additional intra-species identification experiments. For such experiments the relevance of same-species-examples is much larger than that of examples from other classes: the non-causality assumption implies that the intra-class phenotype-genotype correlations differ from those of inter-class correlation. Inter-species correlation may provide valuable information regarding the correlations that exist between elements in the genotype or phenotype vector, but probably cannot predict the relevancy of an intra-species SNP to some visual trait. For the bird dataset intra-species experiments, at each test a pair of genetic markers (from the same species), and a pair of images are provided. Matching is done for both pairs simultaneously providing additional evidence.

The task consists of deciding the correct matching between two sequences $\{x_1, x_2\}$ and two images $\{y_1, y_2\}$. The transformations $W_X$ and $W_Y$ are learned using CCA from the training set as before, and both pairs of test markers and images are transformed. Then distances for both matchings are computed by adding the corresponding sequence-image distances:

$$D_{x_1 \leftrightarrow y_1, x_2 \leftrightarrow y_2} = D_{cc}(W_X^T x_1, W_Y^T y_1) + D_{cc}(W_X^T x_2, W_Y^T y_2)$$

$$D_{x_1 \leftrightarrow y_2, x_2 \leftrightarrow y_1} = D_{cc}(W_X^T x_1, W_Y^T y_2) + D_{cc}(W_X^T x_2, W_Y^T y_1)$$

The matching for which the above distance is smaller is chosen. In this second experiment 63% correct matching was achieved (p<0.00003).

For the task of fish image synthesis, focus is placed on predicting the outline (contour) of the fish. A subset of 93 fish images that have the same number of fins, and therefore share similar topologies was identified. 35 control points corresponding to visually identifiable locations in the fish images were then marked manually on each image. These points were placed on visually identifiable locations.

These 35 2D control points constitute the shape model, which is represented as a 70-dimensional vector $S_i$, i=1 ... 93. In addition, for each of the 93 fish, a simple ad-hoc automatic segmentation algorithm was run to identify the set of points defining its contour.

In each image synthesis experiment, a random partition of 82 training and 11 testing images is created. Linear ridge regression [A. E. Hoerl and R. Kennard. Ridge regression: biased estimation for nonorthogonal problems. Technometrics, 12:55-67, 1970.] is used to learn, from the training set, the mapping between the genetic markers $m_i$ and the shape model $s_i$. The regularization value of the ridge regression is set to some parameter ($\eta=0.05$) times the largest eigenvalue of the covariance matrix of $m_i$.

To synthesize the predicted contour for an unseen genotype $m_{new}$, the shape $s_{new}$ is predicted according to the learned regression formula, and the training example $m_{nearest}$ which is closest genetically to $m_{new}$ is identified. The contour of this nearest species is then warped to create the predicted contour. This warping is performed by applying a thin-plate-spline warp [F. L. Bookstein. Principal warps: thin-plate splines and the decomposition of deformations. IEEE Transactions on Pattern Analysis and Machine Intelligence, 11(6):567-585, June 1989.] which is computed in accordance with the matching points $s_{nearest}$ and $s_{new}$.

To evaluate the quality of the contour reconstruction results, a simple distance measure is applied between the original and predicted contour. For each point on the original contours the distance to the closest point in the predicted one is measured. This score is averaged along all contour points and all 11 testing contours. The mean error obtained for the contour prediction is 3.4% of the image width (standard deviation of 0.6%, measured across 100 repetitions), compared to 6.3% (standard deviation of 5%) obtained by randomly picking one of the training contours as the prediction.

The experiments presented herein demonstrate that images can be identified and predicted by examining small sequences of an animal's genome. The use of the COI gene and microsatellites makes the results more definite by eliminating the possibility of causal genotype-phenotype relations that have been the focus of previous work. Several applications are made possible by further development of such capabilities, such as predicting the appearance of extinct animals for which tissues are available and forensic applications including the identification of suspects by matching DNA evidence to surveillance video or even the synthesis of their portraits from such evidence. The methods employed here can be transferred to non-vision related tasks as well. For example, given a data-set of successfully recovered patients, where for each patient genetic markers and records of treatment are available, models suggesting the suitability of treatment for new patients may be constructed without identifying the underlying mechanisms or focusing on relevant genes.

It will be appreciated by persons skilled in the art that the present invention is not limited by what has been particularly shown and described hereinabove. Rather the scope of the present invention includes both combinations and subcombinations of the various features described hereinabove as well as modifications and variations thereof which would occur to persons skilled in the art upon reading the foregoing description and which are not in the prior art.

The invention claimed is:

1. A method for statistical mapping between genetic information and facial image data, the method comprising:
   collecting a multiplicity of sets of genetic information and matching facial image data representing a multiplicity of individuals;
   representing said genetic information of each of said multiplicity of individuals as a first multidimensional representation;
   representing said facial image data of each of said multiplicity of individuals as a second multidimensional representation; and
   inferring correlative, non-causal, statistical relationships between said first multidimensional representations and said second multidimensional representations.

2. A method for mapping between genetic information and facial image data according to claim 1 and wherein said inferring non-causal statistical relationships excludes inferring causal statistical relationships.

3. A method for mapping between genetic information and facial image data according to claim 1 and wherein said first representation employs at least one of the following methods:
   representing nucleotide sequences of length n as vectors of length 4n wherein each element depicts the number of occurrences of each nucleotide at a specific sequence location in said genetic information;
   representing STR data of n loci as vectors of length 2n wherein each element depicts either the lower or the higher repetition number at one locus in said genetic information;
   representing allele information of n loci, each having a multiplicity of $\gamma_i$, i=1 . . . n alleles as vectors of length $$\sum_{i=1}^{n} \gamma_i$$

wherein each vector element denotes the number of times each allele is present in said genetic information; and
   representing said genetic information implicitly by providing a similarity function between said genetic information arising from every two individuals.

4. A method for mapping between genetic information and facial image data according to claim 1 and wherein said second representation employs at least one of the following algorithms:
   detection of a face region within said facial image data by using a learned template; and
   alignment of said face region by the detection of a set of fiducial points.

5. A method for generating a facial image based on genetic information, the method comprising:
   providing results of statistical mapping between genetic information and facial image data including face shape and facial texture information produced by inferring correlative, non-causal, statistical relationships between first multidimensional representations of said genetic information and second multidimensional representations of said facial image data for a multiplicity of persons;
   applying said results of said statistical mapping to genetic information obtained from an individual not necessarily being an individual whose genetic information is used for inferring said statistical relationships, thereby to obtain facial image data including at least face shape information for said individual; and
   employing said facial image data including face shape and facial texture information to generate said facial image of said individual.

6. A method for generating a facial image based on genetic information according to claim 5 and wherein said facial image data of each of said multiplicity of persons also includes facial texture information.

7. A method for generating a facial image based on genetic information according to claim 5 and wherein:
   said second multidimensional representation employs at least one of the following algorithms:
      detection of a face region within said facial image data by using a learned template; and
      alignment of said face region by the detection of a set of fiducial points, and
   said second multidimensional representation of said facial image data of each of said multiplicity of persons and a multidimensional representation of facial image data of said individual includes at least one of the following representations:
      a shape vector comprising a multiplicity of elements each indicating a location of a feature point or a contour point in said facial image data; and
      a texture vector comprising a multiplicity of elements each indicating an image measurement at one image location of said facial image data.

8. A method for generating a facial image according to claim 7 and wherein said statistical mapping employs at least one of the following algorithms:
   regularized linear regression of said shape vector; and
   regularized linear regression of said texture vector.

9. A method for generating a facial image according to claim 7 and wherein said applying the results of said mapping employs at least one of the following algorithms:
- use of linear regression models for recovering said shape vector of said individual; and
- use of linear regression models for recovering said texture vector of said individual.

10. A method for generating a facial image according to claim 7 and wherein said employing said facial image data including face shape and facial texture included in said facial image data of said individual employs thin plate spline warping of said texture vector of said individual with in accordance with said locations of said shape vector of said individual.

11. A method for generating a facial image according to claim 5 and wherein said statistical mapping employs at least one of the following algorithms:
- regularized linear regression of said face shape information; and
- regularized linear regression of said facial texture information.

12. A method for generating a facial image according to claim 5 and wherein said applying the results of said mapping employs at least one of the following algorithms:
- use of linear regression models for at least one of recovering, generating and predicting said face shape information included in said facial image data of said individual; and
- use of linear regression models for recovering said facial texture information included in said facial image data of said individual.

13. A method for generating a facial image according to claim 5 and wherein said employing said facial image data including face shape and facial texture included in said facial image data of said individual employs thin plate spline warping of said facial texture information of said individual in accordance with said face shape information of said individual.

14. A method for selecting a facial image corresponding to an individual from facial images of a plurality of persons based on genetic information of said individual, the method comprising:
- providing results of statistical mapping between genetic information and facial image data produced by inferring non-causal (correlative) statistical relationships between first multidimensional representations of said genetic information and second multidimensional representations of said facial image data for a multiplicity of individuals, not necessarily including said individual and said plurality of persons; and
- applying said results of said statistical mapping to genetic information obtained from said individual and to said facial images of said plurality of persons, thereby to select said facial image of said individual from among said facial images of said plurality of persons.

15. A method for selecting a facial image according to claim 14 and wherein said facial image data of each of said plurality of persons is represented as a multidimensional representation.

16. A method for selecting a facial image according to claim 15 and wherein:
- said multidimensional representation of said facial image data of each of said plurality of persons employs at least one of the following algorithms:
  - detection of a face region within said facial image data by using a learned template; and
  - alignment of said face region by the detection of a set of fiducial points, and
- said multidimensional representation of said facial image data of each of said plurality of persons includes at least one of the following representations:
  - a vector containing a multiplicity of histograms of image gradients at a multiplicity of image locations; and
  - a vector containing a multiplicity of histograms of local-binary-patterns obtained at a multiplicity of image locations.

17. A method for selecting a facial image according to claim 14 and wherein said inferring of statistical relationships employs at least one of the following algorithms:
- Canonical Correlation Analysis;
- Kernel Canonical Correlation Analysis;
- Nearest Neighbor Transfer;
- Generalized Nearest Neighbor Transfer;
- Inverse Nearest Neighbor Transfer;
- Inverse Generalized Nearest Neighbor Transfer;
- identification based on the structure of recovered phylogenetic-trees;
- statistical classifier learning of multidimensional representations each containing information from said first multidimensional representation and said second multidimensional representation;
- Common Discriminant Feature Extraction;
- Maximal Margin Robot; and
- Preference Margin Optimization.

18. A method for selecting a facial image according to claim 14 and wherein selecting said facial image of said individual from among said facial images of said plurality of persons employs at least one of the following methods:
- transformation of said facial image data and said genetic information using transformations obtained by employing Canonical Correlation Analysis;
- transformation of said facial image data and said genetic information using transformations obtained by employing Kernel Canonical Correlation Analysis;
- selection based on minimal $D_{L_1}$ distance;
- selection based on minimal $D_{CoL_1}$ distance;
- selection based on minimal $D_{L_2}$ distance;
- selection based on minimal $D_{CoL_2}$ distance;
- selection based on minimal $D_C$ distance;
- selection based on minimal $D_{CC}$ distance;
- selection based on the Nearest Neighbor Transfer decision rule;
- selection based on the Generalized Nearest Neighbor Transfer decision rule;
- selection based on the Inverse Nearest Neighbor Transfer decision rule;
- selection based on the Inverse Generalized Nearest Neighbor Transfer decision rule;
- selection based on examining said genetic information obtained from said individual and said facial images of said plurality of persons within the context of phylogenetic trees constructed from said first multidimensional representations of said genetic information and said second multidimensional representations of said facial image data for said multiplicity of individuals;
- selection based on applying classification rules to multidimensional representations each containing information from said first multidimensional representation and said second multidimensional representation;
- transformation of said facial image data and said genetic information using transformations obtained by employing Common Discriminant Feature Extraction;
- selection based on the Maximal Margin Robot matching score; and
- selection based on the Preference Margin Optimization matching score.

* * * * *